(12) United States Patent
Park et al.

(10) Patent No.: US 9,864,104 B2
(45) Date of Patent: *Jan. 9, 2018

(54) BLEND PREPARED BY MIXING A PREPOLYMER AND A VINYL MONOMER AND A POLYMER SHEET OBTAINED THEREFROM

(71) Applicant: ELECTRONICS AND TELECOMMUNICATIONS RESEARCH INSTITUTE, Daejeon (KR)

(72) Inventors: Seung Koo Park, Daejeon (KR); Jung Jin Ju, Daejeon (KR); Suntak Park, Daejeon (KR); Jong-Moo Lee, Daejeon (KR); Min-su Kim, Daejeon (KR); Jin Tae Kim, Daejeon (KR); Joong-Seon Choe, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/918,617

(22) Filed: Oct. 21, 2015

(65) Prior Publication Data

US 2016/0041306 A1   Feb. 11, 2016

Related U.S. Application Data

(62) Division of application No. 14/248,226, filed on Apr. 8, 2014, now Pat. No. 9,201,169, which is a division of application No. 12/634,625, filed on Dec. 9, 2009, now Pat. No. 8,716,403.

(30) Foreign Application Priority Data

Dec. 10, 2008 (KR) .................. 10-2008-0125325
Oct. 22, 2009 (KR) .................. 10-2009-0100772

(51) Int. Cl.
| | | |
|---|---|---|
| C07C 43/29 | (2006.01) |
| G02B 1/04 | (2006.01) |
| C07C 43/225 | (2006.01) |
| C07D 209/48 | (2006.01) |
| C08G 73/10 | (2006.01) |
| C08J 5/18 | (2006.01) |
| C08L 23/02 | (2006.01) |
| C08L 79/08 | (2006.01) |
| G02B 6/122 | (2006.01) |
| G02B 6/138 | (2006.01) |

(Continued)

(52) U.S. Cl.
CPC ............ G02B 1/045 (2013.01); C07C 43/225 (2013.01); C07C 43/29 (2013.01); C07D 209/48 (2013.01); C08F 214/186 (2013.01); C08G 73/1042 (2013.01); C08J 5/18 (2013.01); C08L 23/02 (2013.01); C08L 79/08 (2013.01); G02B 6/02033 (2013.01); G02B 6/1221 (2013.01); G02B 6/138 (2013.01); C07C 2601/14 (2017.05); C07C 2602/48 (2017.05); C08J 2371/02 (2013.01); C08J 2379/08 (2013.01)

(58) Field of Classification Search
CPC .. C07C 43/29; C07D 209/48; C08G 73/1042; C08J 5/18; C08L 23/02; C08L 79/08
USPC ................... 525/132, 418, 420, 461, 534
See application file for complete search history.

(56) References Cited

U.S. PATENT DOCUMENTS

| | | |
|---|---|---|
| 5,760,139 A | 6/1998 | Koike et al. |
| 6,946,534 B2 | 9/2005 | Kim et al. |
| 7,538,160 B2 | 5/2009 | Schorzman et al. |

(Continued)

FOREIGN PATENT DOCUMENTS

| | | |
|---|---|---|
| JP | 2005-105115 A | 4/2005 |
| JP | 2006-154417 A | 6/2006 |

(Continued)

OTHER PUBLICATIONS

Yong Ku Kwon et al., "Organic-inorganic hybrid materials for flexible optical waveguide applications", Journal of material chemistry, 2008, vol. 18, pp. 579-585.

*Primary Examiner* — Edward Cain
(74) *Attorney, Agent, or Firm* — Rabin & Berdo, P.C.

(57) ABSTRACT

Disclosed is a blend prepared by mixing a prepolymer and a vinyl monomer, wherein the prepolymer is prepared by a condensation reaction between a first compound represented by the formula Ar—H, where Ar comprises (a) a crosslinkable moiety at one end, (b) a moiety selected from the group consisting of —O—, —S—, —COO—, —CO—, —COS—, —SO$_2$—, and —NH—, and (c) one or two repeating units selected from the group consisting of:

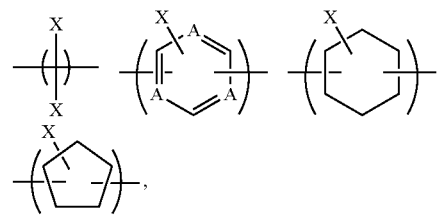

where A is carbon or nitrogen, and X is hydrogen or halogen; and a second compound consisting of an aromatic moiety. Additionally disclosed is a polymer sheet that is a crosslinked product composed of the blend.

4 Claims, 8 Drawing Sheets

(51) Int. Cl.
*G02B 6/02* (2006.01)
*C08F 214/18* (2006.01)

(56) References Cited

U.S. PATENT DOCUMENTS

| | | | |
|---|---|---|---|
| 8,716,403 B2* | 5/2014 | Park | C07C 43/225 |
| | | | 525/132 |
| 9,201,169 B2* | 12/2015 | Park | C07C 43/225 |
| 2003/0181633 A1 | 9/2003 | Blomquist et al. | |
| 2005/0106416 A1 | 5/2005 | Casasanta et al. | |
| 2005/0265686 A1 | 12/2005 | Nishichi et al. | |
| 2008/0293903 A1 | 11/2008 | Petrucci-Samija et al. | |

FOREIGN PATENT DOCUMENTS

| | | |
|---|---|---|
| JP | 2006-154418 A | 6/2006 |
| KR | 10-2004-0006591 A | 1/2004 |
| KR | 10-2004-0006592 A | 1/2004 |
| KR | 10-2005-0060639 A | 6/2005 |
| KR | 10-2006-0110388 A | 10/2006 |
| KR | 10-2007-0108354 A | 11/2007 |
| KR | 10-2008-0097384 A | 11/2008 |

* cited by examiner

BLEND PREPARED BY MIXING A PREPOLYMER AND A VINYL MONOMER AND A POLYMER SHEET OBTAINED THEREFROM

CROSS-REFERENCE TO RELATED PATENT APPLICATION

This is a divisional of co-pending U.S. application Ser. No. 14/248,226 filed Apr. 8, 2014, which is a divisional of U.S Pat. No. 8,716,403 (U.S. application Ser. No. 12/634,625, filed Dec. 9, 2009). This application claims the benefit of Korean Patent Application Nos. 10-2008-0125325, filed on Dec. 10, 2008, and 10-2009-0100772, filed on Oct. 22, 2009, in the Korean Intellectual Property Office, the disclosures of which are incorporated herein in their entirety by reference.

BACKGROUND OF THE INVENTION

1. Field of the Invention

The present invention relates to a material for a flexible thick film optical waveguide for optical interconnection and a method of preparing the same, and more particularly, to a compound used to prepare a thick film optical waveguide having a thickness of several tens of μm or greater, a prepolymer, a blend, and a polymer sheet obtained therefrom, and an optical waveguide for optical interconnection.

2. Description of the Related Art

Polymer materials for optical waveguides include a large amount of fluorine in order to reduce optical loss in optical communication bands during the fabrication of waveguides. Polymer materials have an intrinsic absorption area based on vibrations of C—H, O—H, and N—H bonds. Secondary and tertiary harmonic overtones of the vibrations which are within a near infrared region, i.e., optical communication bands, directly cause optical loss. The overtone absorption of C—H bond stretching vibrations in hydrocarbon polymers is drastically reduced by replacing C—H with C—F, C—Cl, and C—H$^2$ because the harmonics of the C—F, C—Cl, and C—H$^2$ bonds are longer-than that of the C—H bond and are farther from the communication bands, thereby reducing optical absorption in optical communication bands. In particular, a C—F bond may significantly reduce optical loss in the optical communication bands ranging from 1.1 to 1.7 μm. If a C—H bond is replaced by a C—F bond in a polymer to reduce optical loss, polymer solubility may increase so that an optical waveguide may be deformed by a solvent.

Organic materials used for conventional optical waveguides may be solid or liquid. A solid material is dissolved in a proper solvent for fabrication. Thus, there is a need to remove the solvent during the formation of a film. The solid polymer material is formed of an aromatic moiety, solidified after being synthesized, and has a high molecular weight. Thus, the solid polymer has a high viscosity when dissolved. In spin coating that is generally used in the fabrication of a polymer optical waveguide, the high viscosity may affect spin coating process, and thus the increase in the concentration of a polymer solution is limited. Even though the polymer solution is coated to a high thickness due to the high viscosity, it is difficult to obtain a thick film since the solvent is evaporated during the formation of the film. On the other hand, if a polymer solution with a low concentration is used, spin coating is efficiently performed but it is more difficult to obtain a thick film. In order to obtain a thick polymer film using a polymer solution, casting using a doctor-knife may be used instead of spin coating. However, in general, spin coating is used on a silicon wafer in the preparation of an optical waveguide since surface roughness achieved by spin coating is less than that achieved by the doctor-knife. The surface roughness of the optical waveguide is closely related to propagation loss. Since an optical waveguide film prepared using a polymer solution has a high molecular weight and an aromatic moiety, a thick film optical waveguide has excellent mechanical properties.

On the other hand, a liquid material may be simply used in a process of fabricating an optical waveguide. A conventional liquid type polymer material is formed of an aliphatic moiety having a low molecular weight, i.e., an average molecular weight of 1000 or less. Since the molecular weight is not easily increased by a crosslinking process, it is difficult to maintain the shape of the optical waveguide film, and thus a substrate such as a silicon wafer is required. A material mostly composed of aliphatic moieties has poor elasticity and strength, thereby having poor mechanical properties.

As a liquid material for an optical waveguide, photo crosslinkable organic materials with low molecular weight and aliphatic moiety have been developed. Thus, many researches on the variation of optical properties with their combinations have been conducted. An optical waveguide film is formed by UV-curing right after spin coating the photo crosslinkable material. As the UV-curing process proceeds, molecular fluidity decreases, and thus the increase in the molecular weight of the optical waveguide film is limited. This limitation deteriorates the mechanical characteristics of the film. Since the thickness of a film depends on a viscosity of a liquid material during spin coating, and the increase in the viscosity of a low molecular weight liquid is limited, it is difficult to obtain a thick film and to control the thickness of the film.

In order to secure flexibility of an optical waveguide, an organic polymer may be used as a material for forming the optical waveguide. An aliphatic moiety is more efficiently used rather than an aromatic moiety in consideration this flexibility. A siloxane-based material containing silicon may be used in order to secure flexibility of the film. In this regard, organic-inorganic hybrid materials are mainly obtained by siloxane reaction between silane and diol. If the siloxane reaction is not completely performed, optical loss by hydroxyl moieties may be caused. Organic materials containing a large amount of aliphatic hydrocarbon or organic-inorganic hybrid materials containing silicon have high flexibility, but poor elasticity, so that mechanical properties thereof such as tensile strength, abrasion resistance, fatigue resistance, and bending strength may be deteriorated. In order to improve these poor mechanical properties, there is a need to increase the molecular weight of the polymer film or introduce an aromatic moiety thereinto. However, since a polymerized material and a material including a large amount of aromatic moieties may solidify, they need to be dissolved in a solvent to perform spin coating for fabricating a film. This solubilization cause the drawbacks described above.

A variety of organic materials for optical waveguides have been developed. However, most of the conventional materials are not suitable for forming a flexible thick film optical waveguide due to various drawbacks.

SUMMARY OF THE INVENTION

The present invention provides a compound that can be efficiently used to prepare a thick film optical waveguide with low propagation loss in optical communication bands and excellent mechanical properties so as to be used without a substrate.

The present invention also provides a prepolymer, a blend, and a polymer sheet obtained from the compound.

The present invention also provides an optical waveguide for optical interconnection including a polymer sheet prepared from a liquid phase prepolymer.

According to an aspect of the present invention, there is provided a compound represented by Formula 1 below:

Ar—H    Formula 1 wherein Ar comprises a crosslinkable moiety at one end, a moiety selected from the group consisting of —O—, —S—, —COO—, —CO—, —COS—, —SO$_2$—, and —NH—, and one or two repeating units selected from the group consisting of the following repeating units:

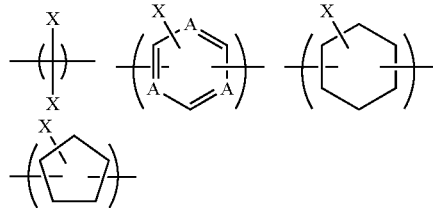

wherein A in the repeating unit is carbon or nitrogen, and X is hydrogen or halogen.

According to another aspect of the present invention, there is provided a prepolymer prepared by condensation reaction between the compound of Formula 1 and one aromatic moiety having one selected from the group consisting of the following structures:

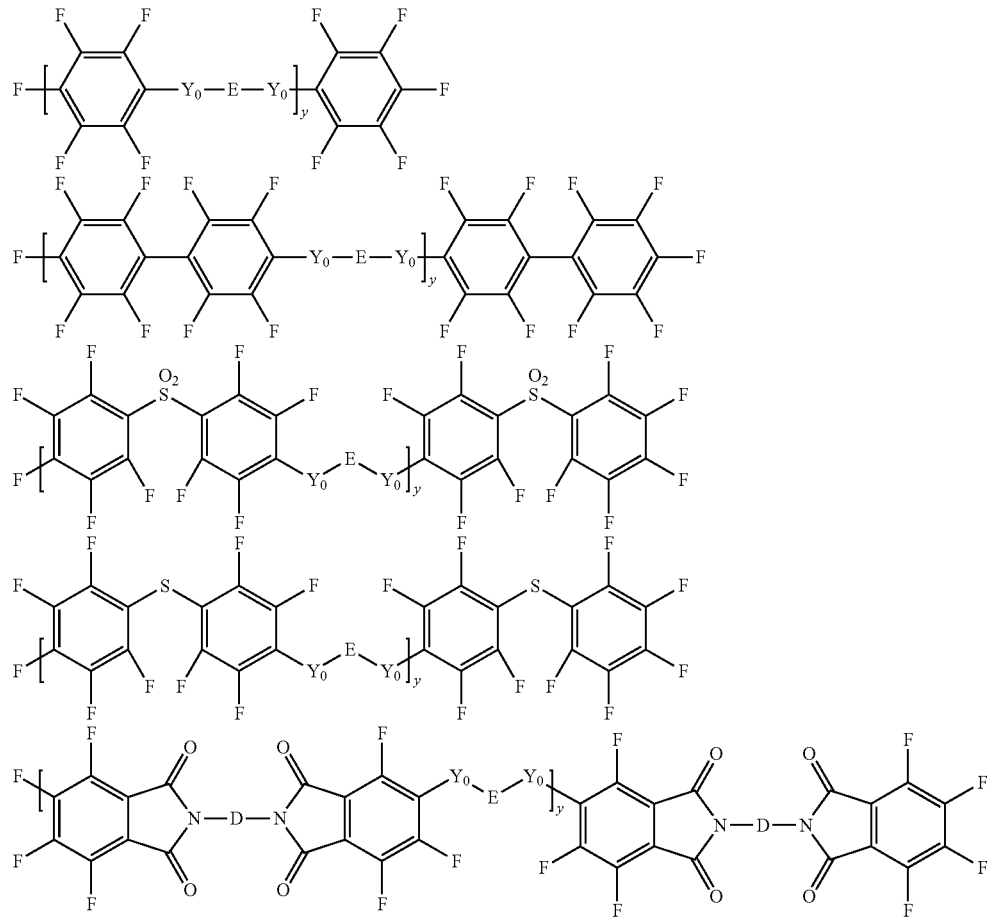

wherein y is an integer from 0 to 1000, $Y_0$ is one selected from the group consisting of —, —O—, —S—, —COO—, —CO—, —COS—, —SO$_2$— and —NH—, wherein the "—" indicates removable, E has one selected from the group consisting of the following structures:

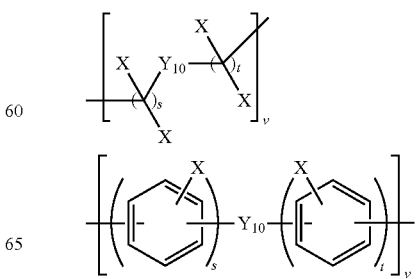

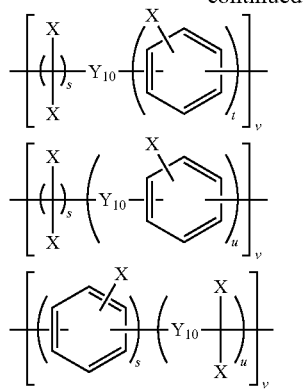

wherein $Y_{10}$ is one selected from the group consisting of —, —O—, —S—, —COO—, —CO—, —COS—, —SO$_2$— and —NH—, s and t are each independently an integer from 1 to 50, u is an integer from 0 to 50, and v is an integer from 1 to 100, and D has one selected from the group consisting of the following structures:

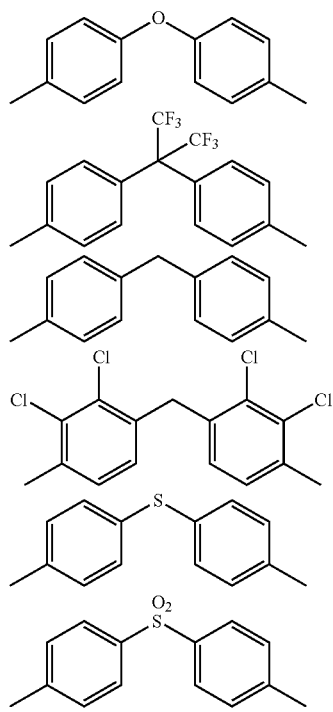

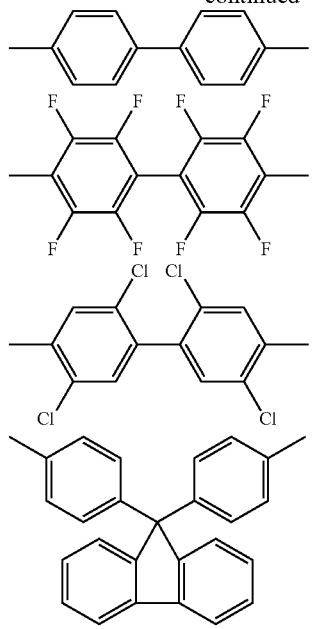

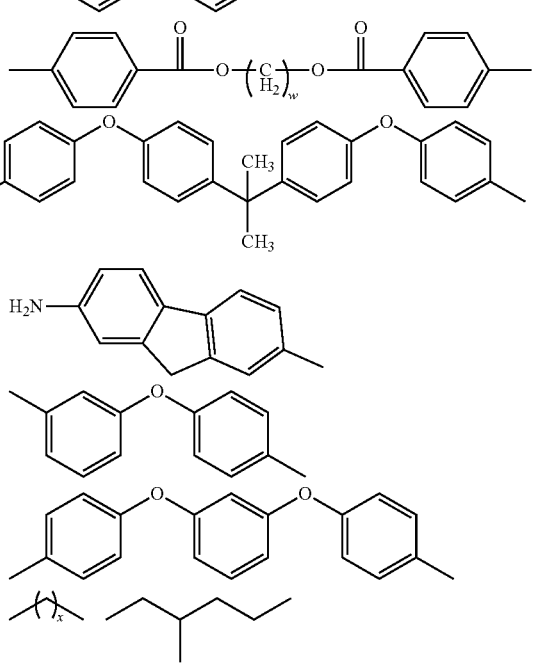

wherein w and x are each independently an integer from 1 to 20.

The prepolymer may be represented by Formula 2 or 3 below:

Formula 2

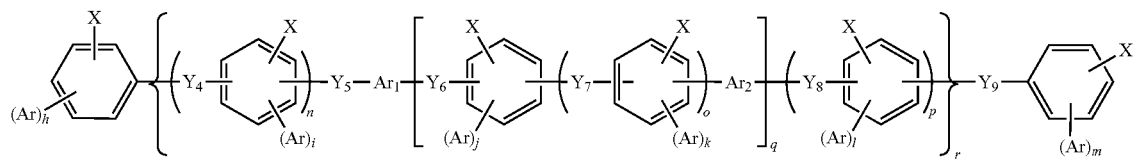

Formula 3

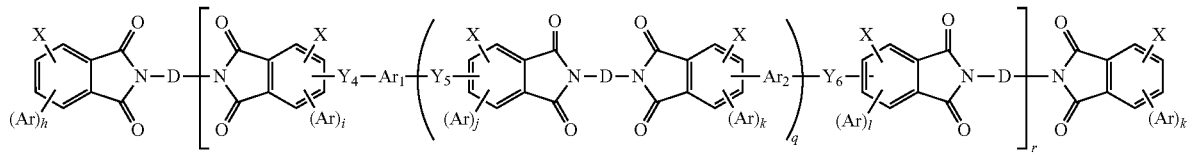

wherein $Y_4$, $Y_5$, $Y_6$, $Y_7$, $Y_8$ and $Y_9$ are each independently one selected from the group consisting of —, —O—, —S—, —COO—, —CO—, —COS—, —SO$_2$— and —NH—, h, i, j, k, l and m are each independently an integer from 0 to 2, n, o, p, q and r are each independently an integer from 0 to 10, and each of $Ar_1$ and $Ar_2$ independently has one selected from the group consisting of the following structure:

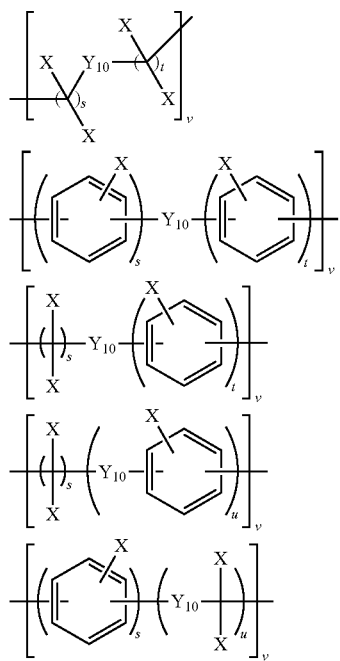

wherein $Y_{10}$ is one selected from the group consisting of —, —O—, —S—, —COO—, —CO—, —COS—, —SO$_2$— and —NH—, s and t are each independently an integer from 1 to 50, u is an integer from 0 to 50, and v is an integer from 1 to 100.

The prepolymer may be in a solid or a liquid phase. If the prepolymer has a liquid phase, the viscosity of the prepolymer may be in the range of 1 to $10^7$ cps at a temperature ranging from 0 to 50° C.

According to another aspect of the present invention, there is provided a blend prepared by mixing the prepolymer according to an embodiment of the present invention and a polymer. In this regard, the polymer may be one selected from the group consisting of a photocrosslinkable polymer, a thermocrosslinkable polymer, polyester, polyamide, polyimide, polycarbonate, polyethylene, polymethyl methacrylate, polypropylene and polyether.

According to another aspect of the present invention, there is provided a blend prepared by mixing the prepolymer according to an embodiment of the present invention and a vinyl monomer miscible with the prepolymer. In this regard, the vinyl monomer may be one selected from the group consisting of styrene, 2,3,4,5,6-pentafluoro styrene, divinyl benzene, methyl methacrylate, methyl acrylate, trifluoroacetic acid allyl ester, trifluoroacetic acid vinyl ester, 2,2,2-trifluoroethyl methacrylate, acrylic acid 1,1,1,3,3,3-hexafluoroisopropyl ester, methacrylic acid 1,1,1,3,3,3-hexafluoroisopropyl ester, maleic anhydride, N-methyl maleimide, N-ethyl maleimide, N-propylmaleimide, N-butyl maleimide, N-tert-butyl maleimide, N-pentyl maleimide, N-hexyl maleimide and 1-pentafluorophenylpyrrole-2,5-dione. The viscosity and refractive index of the blend may vary by adjusting the ratio of the vinyl monomer to the prepolymer according to an embodiment of the present invention.

According to another aspect of the present invention, there is provided a polymer sheet including a crosslinked product of the prepolymer or a crosslinked product of the blend according to embodiments of the present invention.

According to another aspect of the present invention, there is provided an optical waveguide for optical interconnection including at least one polymer sheet according to embodiments of the present invention According to another aspect of the present invention, there is provided an optical waveguide for optical interconnection including a core as an optical path, and a cladding covering the core, wherein at least one of the core and the cladding includes at least one polymer sheet according to embodiments of the present invention.

The optical waveguide may further include a base film covering at least a portion of the cladding. The base film may include a polymer. Alternatively, the base film may include at least one polymer sheet defined according to the present invention.

The optical waveguide for optical interconnection may also include a metal sheet or a metal thin film covering at least a portion of the cladding.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
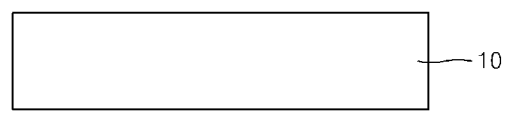
FIGS. 1A to 1F show cross-sectional views of an optical waveguide for optical interconnection at each fabrication step according to an embodiment of the present invention.

The present invention will now be described more fully with reference to the accompanying drawings, in which exemplary embodiments of the invention are shown.

According to an embodiment of the present invention, there is provided a prepolymer having a high fluorine content by replacing a carbon (C)-hydrogen (H) bond in a backbone of a polymer with a carbon (C)-fluorine (F) bond in order to reduce optical loss of a polymer optical waveguide in optical communication bands. The prepolymer may be suitable for spin coating or a doctor-knife process that is widely used in the art. Since the prepolymer may be in a liquid phase, a solvent may not be required. The prepolymer may contain an appropriate ratio of aliphatic moiety to aromatic moieties in order to maintain the liquid phase and to secure excellent mechanical properties after a thick film is formed. Also, the molecular weight of the prepolymer may be controlled in order to control the viscosity. Accordingly, the thickness of the thick film may also be controlled. Even in the case that the prepolymer is in a solid phase, it may be easily dissolved in a vinyl monomer, and thus a solvent may not be required in the formation of the thick film. The prepolymer, whether it is in a liquid phase or in a solid phase, may be miscible with the vinyl monomer, and thus a blend including the prepolymer and the vinyl monomer may be prepared. Since a low molecular weight vinyl monomer acts as a chain extender, the molecular weight of a polymer increases after crosslinking of the prepolymer. In addition, the viscosity and the refractive index may be easily controlled according to the ratio of the prepolymer to the vinyl monomer.

The prepolymer includes an ether-based compound as a repeating unit. The prepolymer may have a copolymerization structure by using a suitable synthesis process as long as the properties suitable for a flexible optical waveguide do not deteriorate. The refractive index may be efficiently controlled by the copolymerization structure. The prepolymer may be designed such that a backbone thereof has a three-dimensional structure in order to improve thermal, chemical, and mechanical characteristics of the thick film formed of the prepolymer. In addition, the compound according to an embodiment of the present invention includes a crosslinkable moiety. Since the crosslinkable moiety is distributed in multidirections in a three-dimensional space, the solubility of the optical waveguide decreases and the molecular weight significantly increases after the crosslinking process. Since three-dimensionally net-like properties may be improved by the crosslinking process, the mechanical characteristics of the obtained thick film are improved and anisotropy of the mechanical characteristics may be reduced. Therefore, the thick film may be used as a material for an optical waveguide without a substrate.

Since conventional polymer optical waveguide thin films have poor mechanical properties, a substrate such as a silicon wafer is required. However, a polymer sheet obtained from the prepolymer according to an embodiment of the present invention and an optical waveguide obtained therefrom have chemical structures providing flexibility. Thus, the shape of the thick film may be maintained in a good condition without using a substrate and a flexible optical waveguide can be fabricated from the prepolymer. The flexible optical waveguide has sufficient flexibility and excellent mechanical characteristics, thereby having excellent fatigue resistance. In addition, the thick film has low optical loss, and thus may be efficiently used as a material for forming the optical waveguide.

The compound according to the present embodiment is represented by Formula 1 below.

$$Ar\text{—}H \qquad \text{Formula 1}$$

In Formula 1, Ar is an aliphatic moiety, an aromatic moiety, or a combination thereof. Ar includes a crosslinkable moiety at one end, a moiety selected from the group consisting of —O—, —S—, —COO—, —CO—, —COS—, —SO$_2$—, and —NH—, and one or two repeating units selected from the group consisting of the following repeating units:

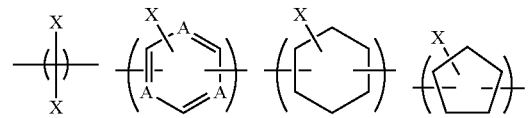

wherein A in the repeating unit is carbon or nitrogen, and X is hydrogen or halogen.

The crosslinkable moiety may have one selected from the group consisting of the following structures.

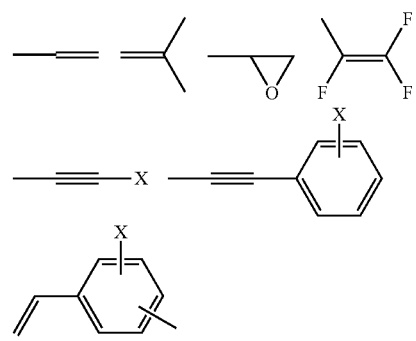

Ar may have one selected from the group consisting of the following structures.

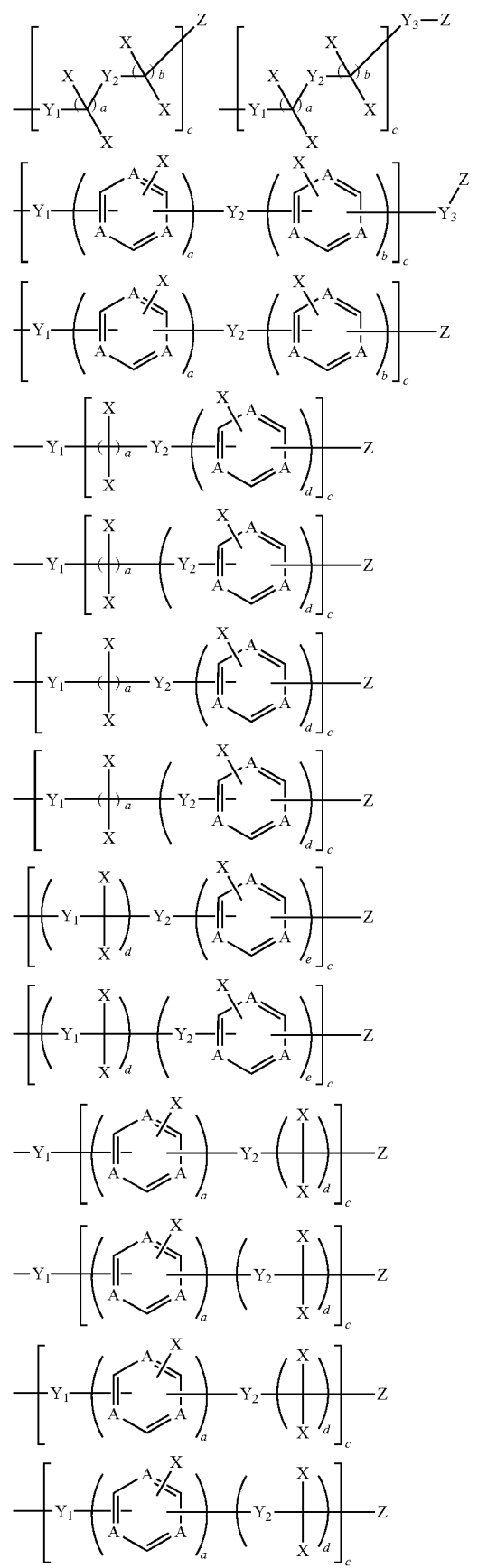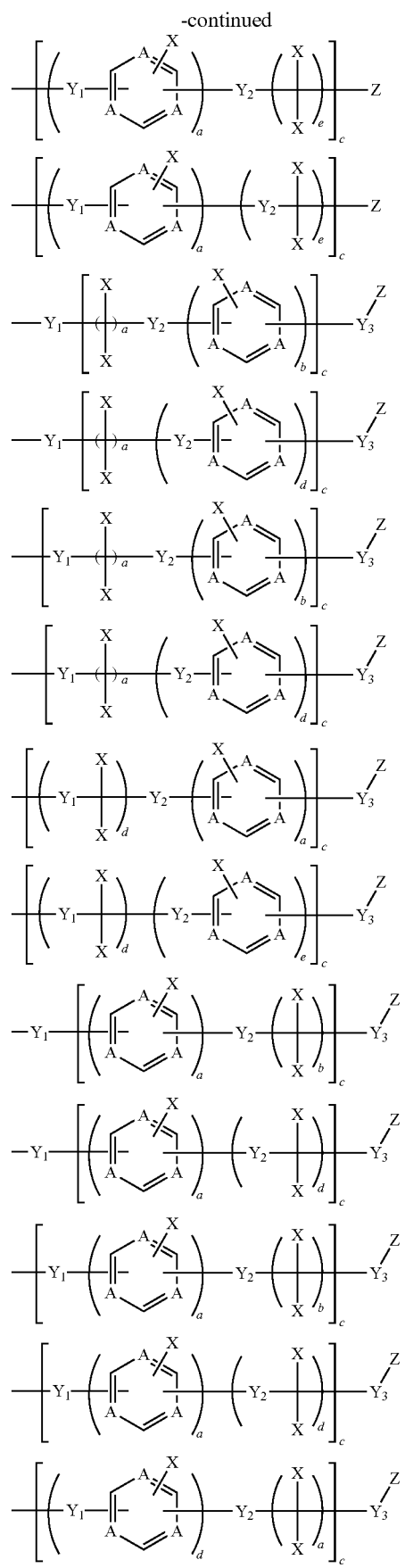

-continued
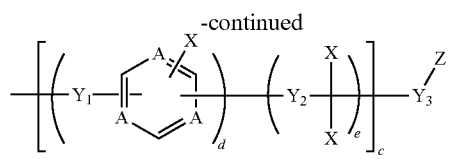
In this regard, A is carbon or nitrogen, X is hydrogen or halogen, $Y_1$, $Y_2$ and $Y_3$ are each independently one selected from the group consisting of —, —O—, —S—, —COO—, —CO—, —COS—, —SO$_2$— and —NH—, Z is a cross-linkable moiety, a, b, d and e are each independently an integer from 1 to 50, and c is an integer from 1 to 100.
Ar may have one selected from the group consisting of the following structures.
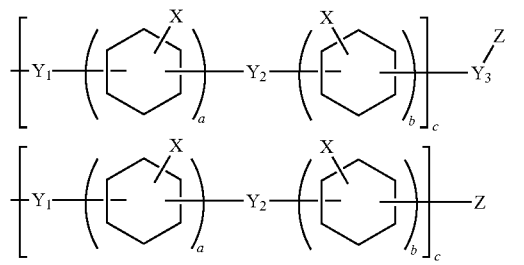
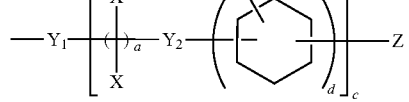
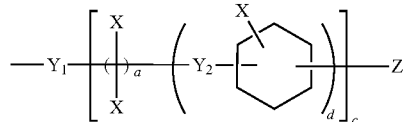
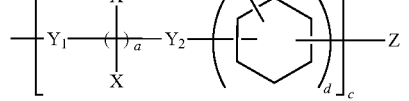
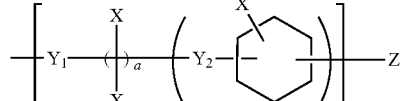
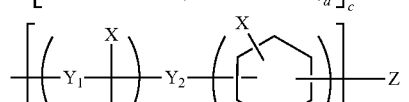
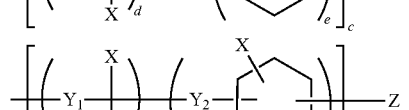
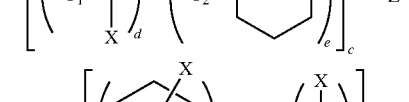
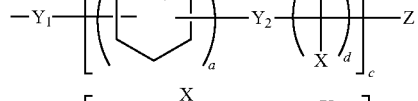
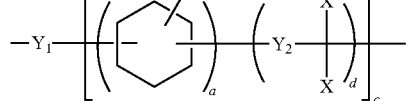
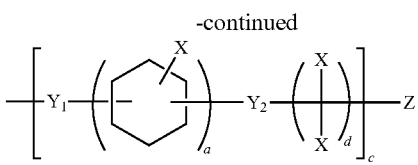
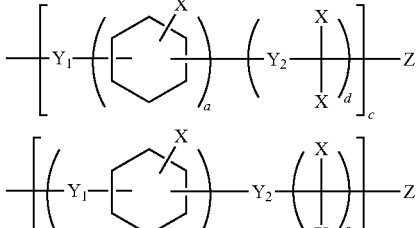
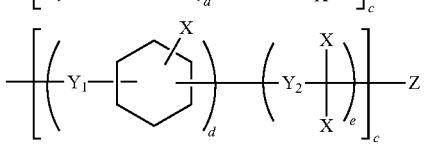
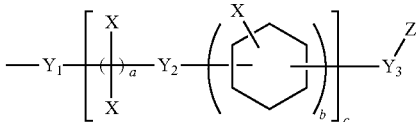
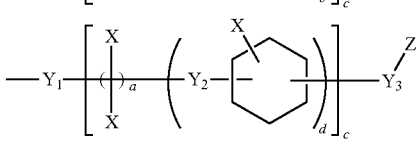
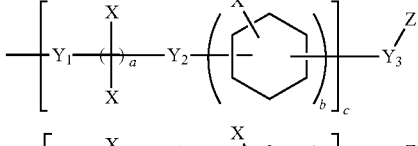
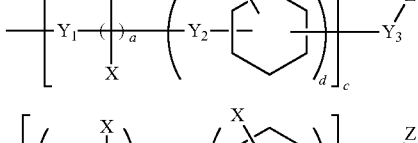
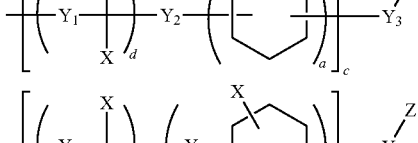
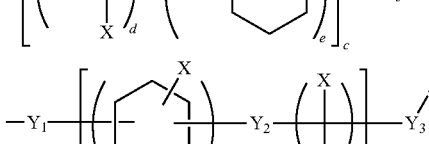
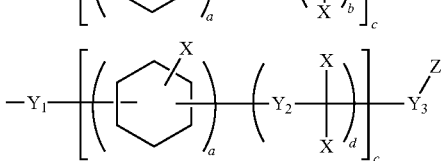
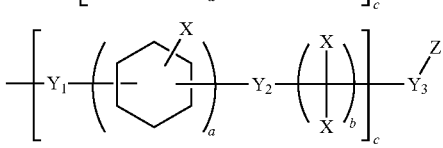

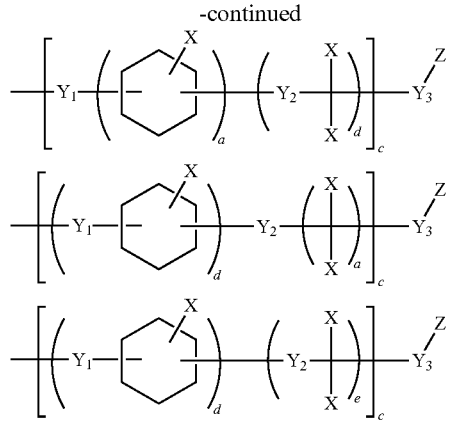
In this regard, X is hydrogen or halogen, $Y_1$, $Y_2$ and $Y_3$ are each independently one selected from the group consisting of —, —O—, —S—, —COO—, —CO—, —COS—, —SO$_2$— and —NH—, Z is a crosslinkable moiety, a, b, d and e are each independently an integer from 1 to 50, and c is an integer from 1 to 100.
Ar may have one selected from the group consisting of the following structures.
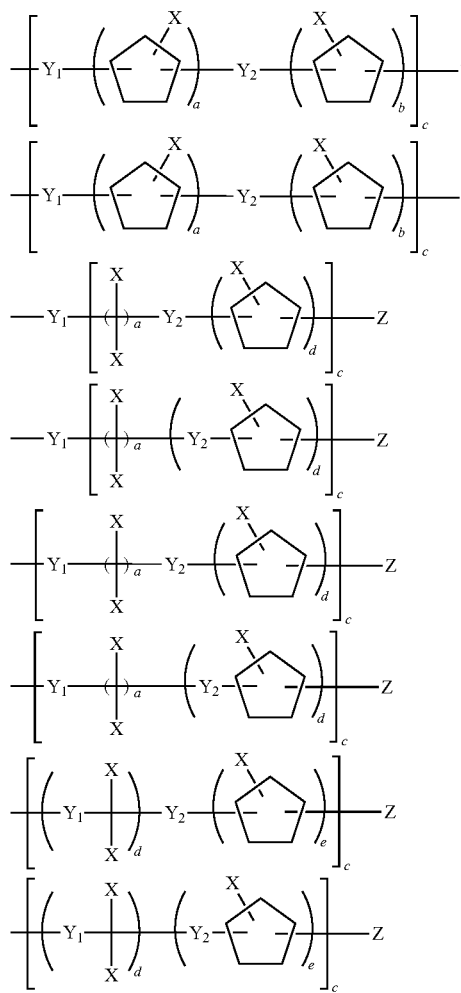
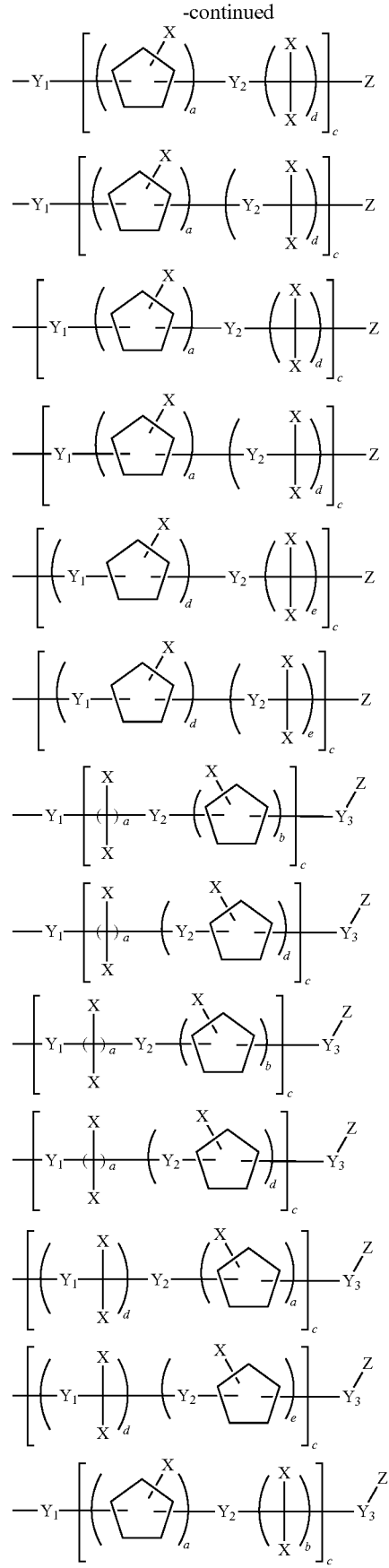

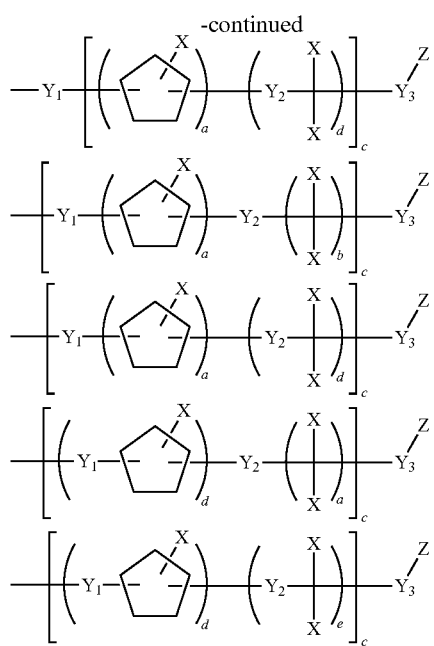

In this regard, X is hydrogen or halogen, $Y_1$, $Y_2$ and $Y_3$ are each independently one selected from the group consisting of —, —O—, —S—, —COO—, —CO—, —COS—, —SO$_2$— and —NH—, Z is a crosslinkable moiety, a, b, d and e are each independently an integer from 1 to 50, and c is an integer from 1 to 100.

Ar may have one selected from the group consisting of the following structures.

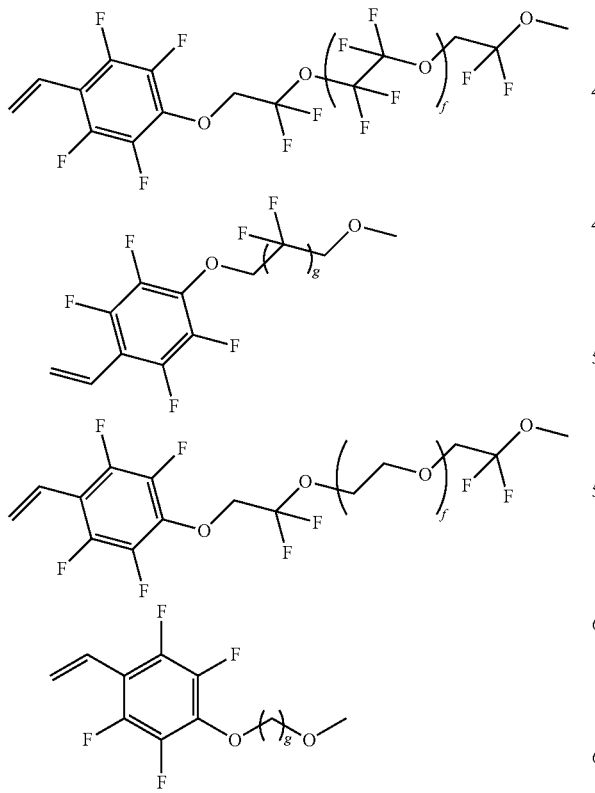

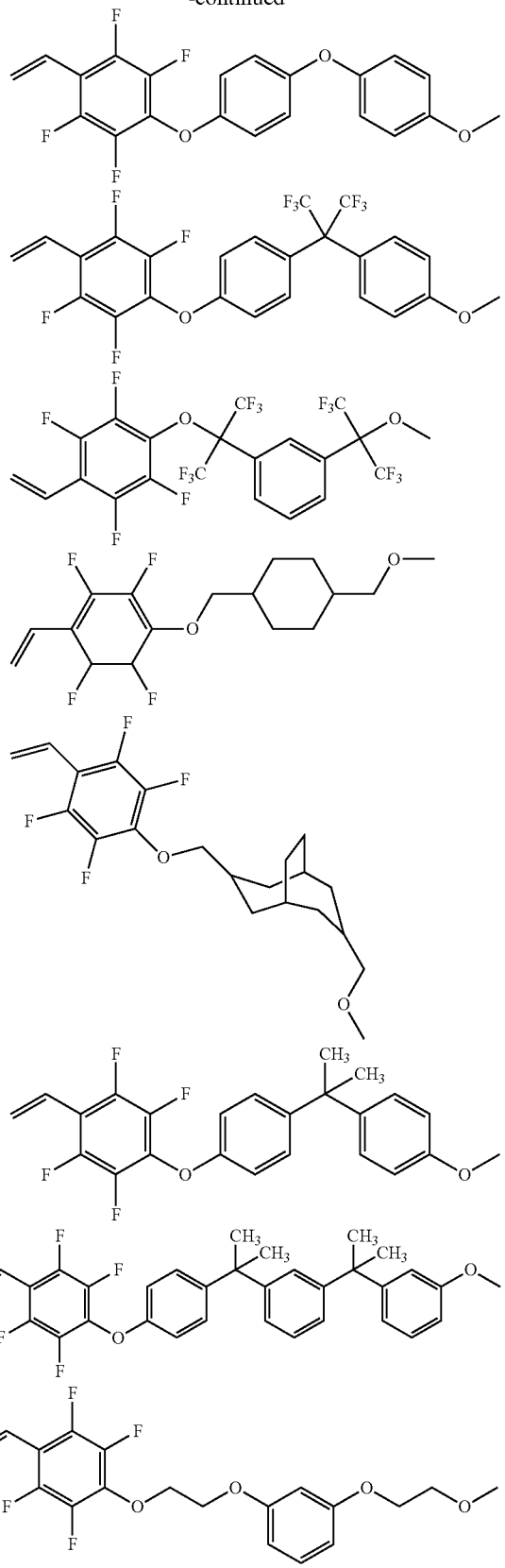

In this regard, f is an integer from 1 to 10, and g is an integer from 1 to 20.

The prepolymer according to the present invention may be prepared by condensation reaction between the compounds according to the present invention as above and aromatic compounds having halogen.

The aromatic moiety having halogen may include one of the following structures. In particular, the aromatic moiety having the halogen may include one or a plurality of the structures selected from the below, in which the plurality of the structures may be physically or chemically mixed.

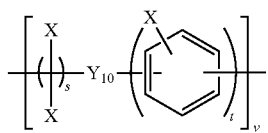

-continued

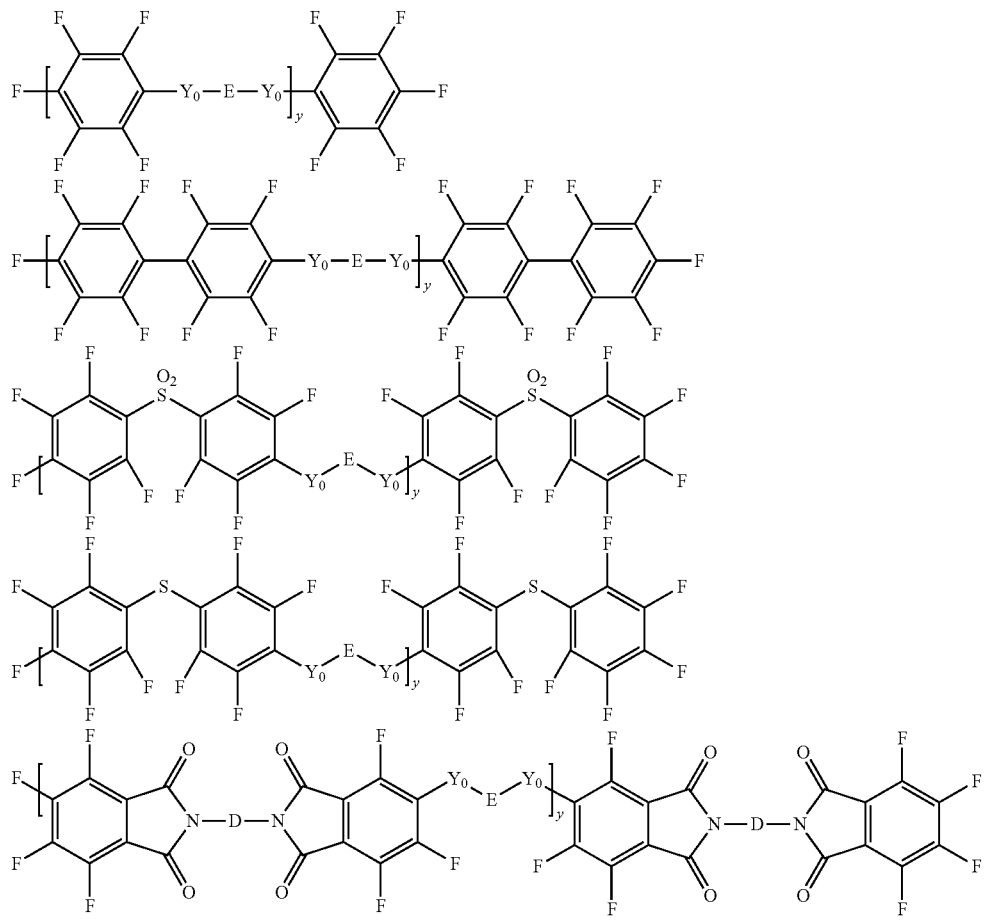

In this regard, y is an integer from 0 to 1000.

$Y_0$ is one selected from the group consisting of —, —O—, —S—, —COO—, —CO—, —COS—, —SO$_2$— and —NH—, E may have one selected from the group consisting of the following structures.

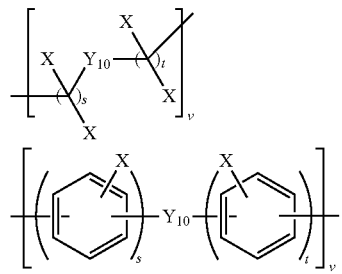

-continued

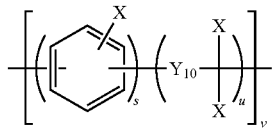

Here, $Y_{10}$ is one selected from the group consisting of —, —O—, —S—, —COO—, —CO—, —COS—, —SO$_2$— and —NH—, s and t are each independently an integer from 1 to 50, u is an integer from 0 to 50, and v is an integer from 1 to 100.

D may have one selected from the group consisting of the following structures. In particular, D may have one or a combination of a plurality of structures selected from the below.

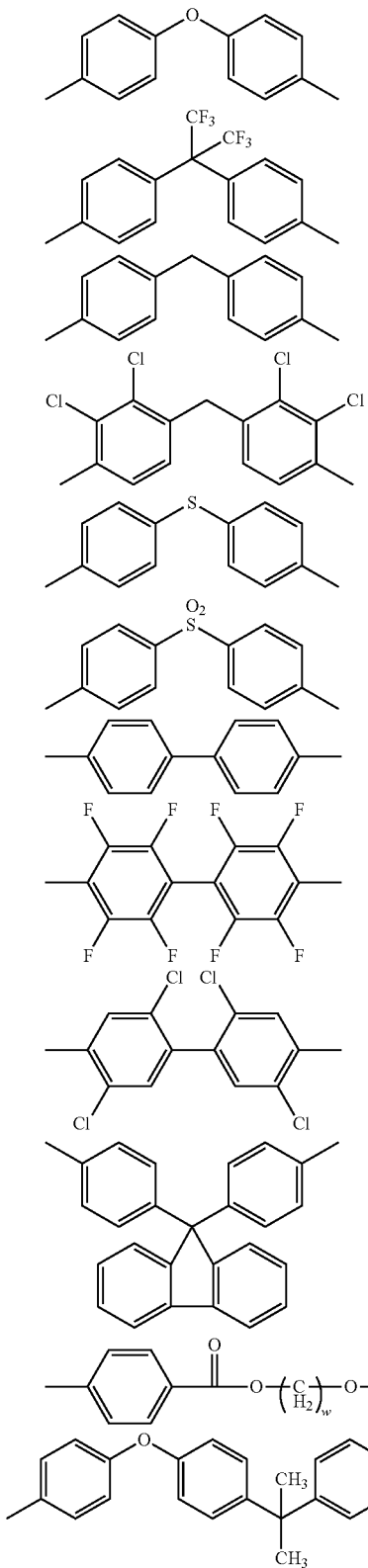

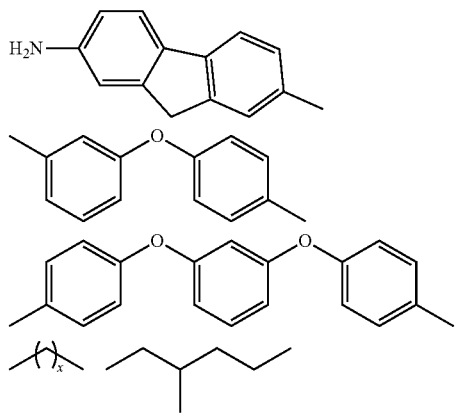

Here, w and x are each independently an integer from 1 to 20.

D is a moiety that may be induced from a compound including an aliphatic or aromatic diamine group capable of reacting with an anhydride moiety to be imidized. Examples of the compound including an aliphatic or aromatic diamine group used to form D are as follows.

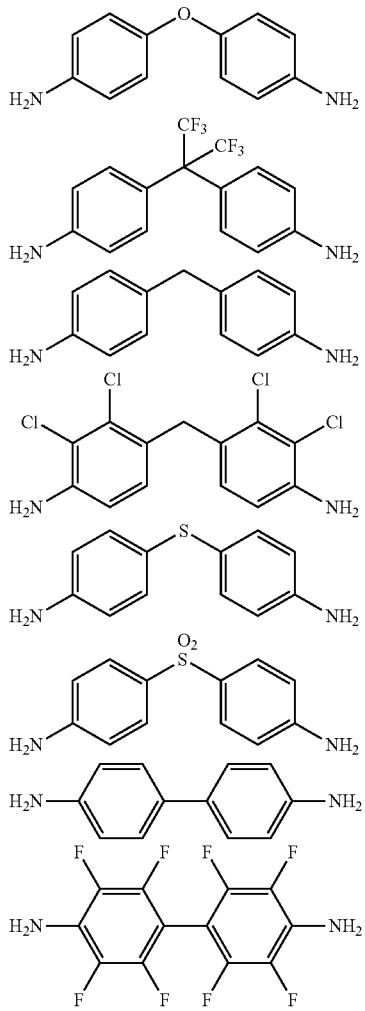

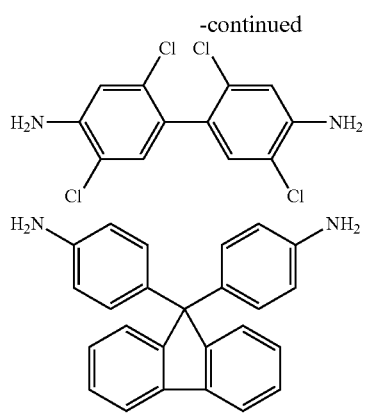

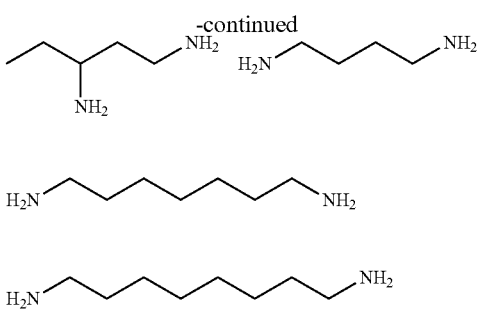

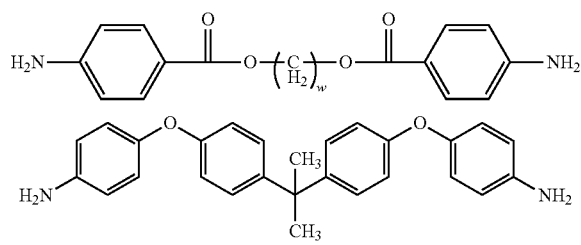

Here, w is an integer from 1 to 20.

The prepolymer may be represented by one of Formula 2 and Formula 3 below.

Formula 2

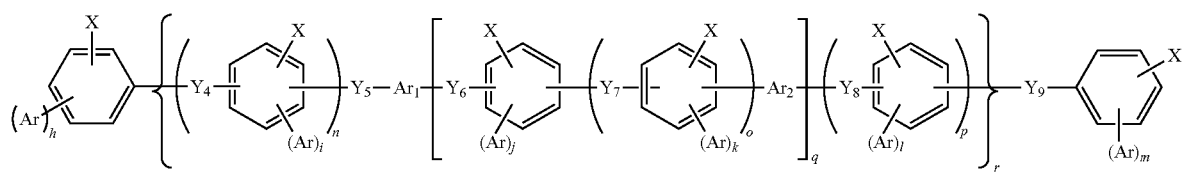

Formula 3

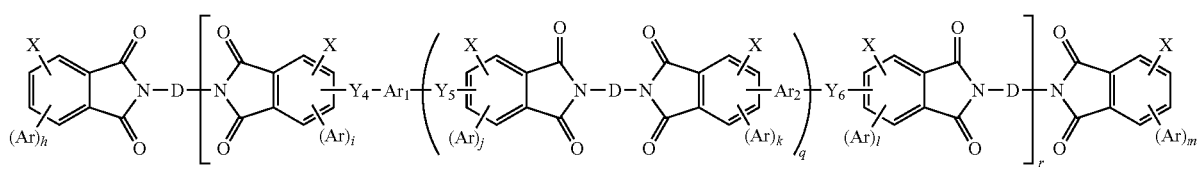

In Formulae 2 and 3, $Y_4$, $Y_5$, $Y_6$, $Y_7$, $Y_8$ and $Y_9$ are each independently one selected from the group consisting of —, —O—, —S—, —COO—, —CO—, —COS—, —SO$_2$— and —NH—, h, i, j, k, l and m are each independently an integer from 0 to 2, n, o, p, q and r are each independently an integer from 0 to 10, and each of $Ar_1$ and $Ar_2$ independently has one selected from the following structures.

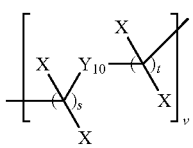

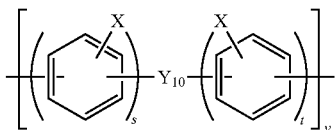

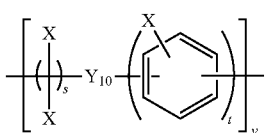

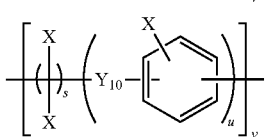

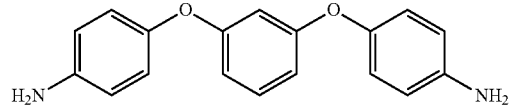

-continued

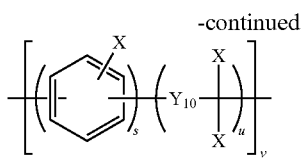

Here, $Y_{10}$ is one selected from the group consisting of —, —O—, —S—, —COO—, —CO—, —COS—, —SO$_2$— and —NH—, s and t are each independently an integer from 1 to 50, u is an integer from 0 to 50, and v is an integer from 1 to 100.

In the compound of Formula 3, D does not have a crosslinkable moiety, and thus the degree of freedom may be significantly increased during the synthesis of compounds according to the present invention.

The prepolymer according to the present invention is prepared by condensation between the compound of Formula 1 and an aromatic compound having halogen. The prepolymer may have a viscosity suitable for the fabrication process of the optical waveguide by controlling the molecular weight and chemical structure. In particular, the prepolymer may have a solid or liquid phase. The liquid phase prepolymer may have a viscosity ranging from 1 to $10^7$ cps at a temperature ranging from 0 to 50° C. In addition, the prepolymer, whether it is in a liquid phase or in a solid phase, may be miscible with the vinyl monomer, and thus a mixture of the prepolymer and the vinyl monomer may be prepared.

Optical properties of the optical waveguide such as a refractive index and optical loss may be controlled based on the chemical structure of the compound used for the synthesis of the prepolymer. In the synthesis of the compound, the solubility of the compound may increase due to the halogen introduced thereinto to control the optical characteristics. In this regard, after forming a sheet (or film) using the prepolymer, the sheet may undergo crosslinking to improve the chemical resistance thereof. For this, about 0.1 to about 10 wt % of a photo-curable initiator or thermosetting initiator based on the total weight of the prepolymer of Formula 2 or 3 may be dissolved in the prepolymer. For example, the concentration of the photo-curable initiator or thermosetting initiator may be in the range of about 0.5 to about 2.5 wt % in the prepolymer. Impurities are removed from the compound of the present invention to which the photo-curable initiator or thermosetting initiator is added by using a filter, and the compound may be coated on a base substrate such as a glass plate, film, and a silicon wafer by using spin coating or a doctor-knife to form a thick film sheet. If the photo-curable initiator is used, the thick film sheet may be exposed in a UV hardening device for about 0.1 seconds to about 20 minutes after forming the thick film sheet. Then, the thick film sheet may be heat-treated under nitrogen at a temperature ranging from about 50 to about 300° C. For example, the heat-treatment may be performed at a temperature raging from about 50 to about 250° C. If the thermosetting initiator is used, heat suitable for reaching the reaction conditions of the crosslinkable moiety is applied thereto. In this regard, the thick film sheet may be heat-treated under nitrogen or under vacuum at a temperature ranging from about 100 to about 500° C. for about 5 minutes or more. For example, the thick film sheet may be heat-treated at a temperature ranging from about 150 to about 350° C. for about 0.5 to 2 hours. The hardened polymer sheet is detached from the substrate, and then a flexible thick film polymer sheet having a thickness ranging from about 50 µm or more may be obtained.

In order to improve bending strength and mechanical properties of the polymer sheet, a polymer film may be used as the base film. The polymer film may be formed of polyester, polyamide, polyimide, polycarbonate, polyethylene, polymethyl methacrylate, polypropylene, or polyether. If the polymer film is used as the substrate, the substrate is not required to be separated from the polymer sheet and may be used as an element of the optical waveguide.

According to another embodiment of the present invention, there is also provided a blend including the prepolymer and a polymer. For example, the blend may include a compound of Formula 2 or 3 and a polymer. In this regard, the polymer may be selected from the group consisting of a photocrosslinkable polymer, a thermocrosslinkable polymer, polyester, polyamide, polyimide, polycarbonate, polyethylene, polymethyl methacrylate, polypropylene and polyether.

As the photocrosslinkable polymer, a polymer represented by Formula 4 below may be used.

Formula 4

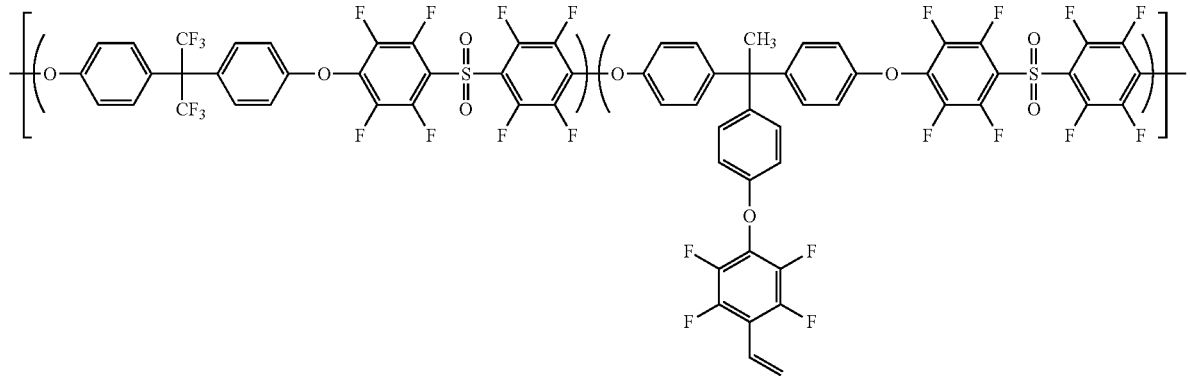

The polymer of Formula 4 is disclosed in Yinguha Qi et al., Chem. Mater., 17, 676-682, 2005.

As the thermocrosslinkable polymer, a polymer represented by Formula 5 may be used.

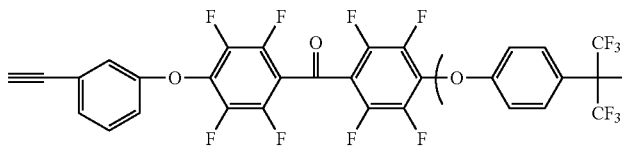
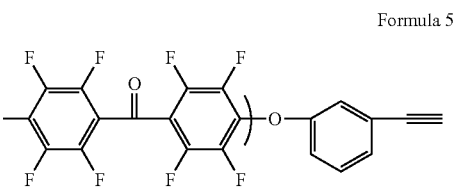

Formula 5

The polymer of Formula 5 is disclosed in Hyung-Jong Lee et al., J. Polym. Sci.; Polym. Chem. Ed., 37, 2355-2361, 1999.

According to another embodiment of the present invention, there is also provided a blend including the prepolymer and a vinyl monomer. For example, the blend may include a compound of Formula 2 or 3 and a vinyl monomer. In this regard, the vinyl monomer may be: a styrene monomer such as 2,3,4,5,6-pentafluoro styrene and divinyl benzene; an acrylic monomer such as methyl methacrylate, methyl acrylate, trifluoroacetic acid allyl ester, trifluoroacetic acid vinyl ester, 2,2,2-trifluoroethyl methacrylate, acrylic acid 1,1,1,3,3,3-hexafluoroisopropyl ester, and methacrylic acid 1,1,1,3,3,3-hexafluoroisopropyl ester; or maleic anhydride, or a maleimide monomer such as N-methyl maleimide, N-ethyl maleimide, N-propylmaleimide, N-butyl maleimide, N-tert-butyl maleimide, N-pentyl maleimide, N-hexyl maleimide, and 1-pentafluorophenylpyrrole-2,5-dione. The vinyl monomer acts as a chain extender to increase the molecular weight of the prepolymer during crosslinking. In addition, the viscosity and the refractive index may be easily controlled via the ratio of the prepolymer to the vinyl monomer.

The prepolymer and the blend according to the present invention may respectively form a first polymer sheet that forms a core as an optical path in an optical waveguide for optical interconnection. Alternatively, the prepolymer and the blend may respectively form a second polymer sheet that forms a cladding covering the core.

The first polymer sheet and the second polymer sheet may have a single layered structure or a stacked structure in which two or more layers are stacked.

In the optical waveguide for optical interconnection, the first polymer sheet and the second polymer sheet respectively include a first sheet formed of the prepolymer or the blend and a second sheet coated on the first sheet and formed of a polymer that is different from that used to form the first sheet. The second sheet may be formed of the prepolymer or the blend according to the present invention. Alternatively, the second sheet may be formed of a flexible polymer such as polyester, polyamide, polyimide, polycarbonate, polyethylene, polymethyl methacrylate, polypropylene or polyether.

In the optical waveguide for optical interconnection, the cladding may be a polymer sheet formed of the prepolymer or the blend according to the present invention, and the core may be a film formed of a photocrosslinkable polymer, a thermocrosslinkable polymer, a photocrosslinkable oligomer, or a thermocrosslinkable oligomer. For example, the photocrosslinkable polymer may be a polymer represented by Formula 4. The thermocrosslinkable polymer may be a polymer represented by Formula 5. In addition, the photocrosslinkable oligomer may be an oligomer represented by Formula 6.

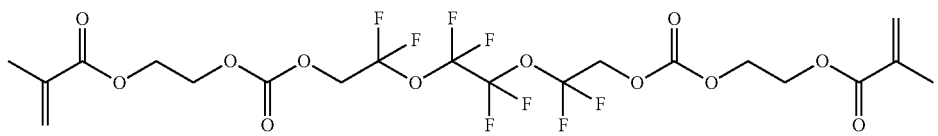

Formula 6

The oligomer of Formula 6 is disclosed in Eunkyoung Kim et al., Chem. Mater., 17, 962-966, 2005.

In addition, the thermocrosslinkable oligomer may be an oligomer represented by Formula 7.

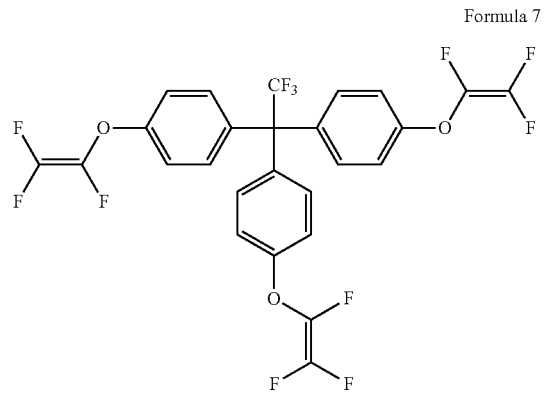 [SMILES: FC(F)=C(F)Oc1ccc(C(c2ccc(OC(F)=C(F)F)cc2)(c2ccc(OC(F)=C(F)F)cc2)C(F)(F)F)cc1]

Formula 7

The oligomer of Formula 7 is disclosed in Dennis W. Smith, Jr. et al., Adv. Mater., 14, 1585-1589, 2002.

As described above, in the optical waveguide for optical interconnection having one of the core and the cladding or both of the core and the cladding that are a polymer sheet formed of the compound or the blend according to the present invention, a polymer base film formed of a flexible polymer such as polyester, polyamide, polyimide, polycarbonate, polyethylene, polymethyl methacrylate, polypropylene or polyether may be coated on at least one portion of the polymer sheet.

In addition, in the optical waveguide for optical interconnection, a metal sheet formed of gold, silver, copper, or aluminum may be coated respectively on at least one portion of the first polymer sheet forming the core and the second polymer sheet forming the cladding. The metal sheet may have a thickness ranging from about 5 nm to about 500 μm and a predetermined pattern with a width ranging from about 1 to about 1000 μm or a plurality of metallic patterns spaced apart from each other by a distance ranging from about 1 to about 1000 µm. Such a metal film may be attached to the surface of the first polymer sheet or the second polymer sheet. Alternatively, in the optical waveguide for optical interconnection including the plurality of the polymer sheets, the metal film may be interposed between the plurality of polymer sheets.

FIGS. 1A to 1F are cross-sectional views of an optical waveguide 100 for optical interconnection according to an embodiment of the present invention, for describing a process for preparing the optical waveguide 100.

Referring to FIG. 1A, a surface 10 is prepared.

The substrate 10 may be a silicon wafer.

Also, the substrate 10 may be formed of a polymer. For example, the substrate 10 may be a polymer film formed of polyester, polyamide, polyimide, polycarbonate, polyethylene, polymethyl methacrylate, polypropylene, or polyether.

Also, the substrate 10 may be formed of a prepolymer according to an embodiment of the present invention. For example, the substrate 10 may be prepared as a polymer sheet by coating the prepolymer and hardening the coated prepolymer. Also, a polymer sheet prepared by coating a blend of the prepolymer and a polymer and hardening the coated blend may be used as the substrate 10. In this regard, the polymer that is blended with the prepolymer may be a photocrosslinkable polymer, a thermocrosslinkable polymer, polyester, polyamide, polyimide, polycarbonate, polyethylene, polymethyl methacrylate, polypropylene or polyether.

In addition, a polymer sheet prepared by coating a blend of the prepolymer and a vinyl monomer and hardening the blend may be used as the substrate 10. The vinyl monomer that is miscible with the prepolymer may be: a styrene monomer such as 2,3,4,5,6-pentafluoro styrene and divinyl benzene; an acrylic monomer such as methyl methacrylate, methyl acrylate, trifluoroacetic acid allyl ester, trifluoroacetic acid vinyl ester, 2,2,2-trifluoroethyl methacrylate, acrylic acid 1,1,1,3,3,3-hexafluoroisopropyl ester, and methacrylic acid 1,1,1,3,3,3-hexafluoroisopropyl ester; or maleic anhydride, or a maleimide monomer such as N-methyl maleimide, N-ethyl maleimide, N-propylmaleimide, N-butyl maleimide, N-tert-butyl maleimide, N-pentyl maleimide, N-hexyl maleimide, and 1-pentafluorophenylpyrrole-2,5-dione.

As described above, if the prepolymer according to the present embodiment is used to prepare the substrate 10, the substrate 10 does not have to be separated after an optical waveguide is prepared.

Figure 1B:
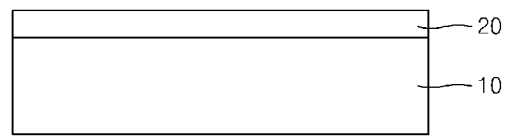

Referring to FIG. 1B, a lower cladding 20 is formed on the substrate 10.

The lower cladding 20 may be formed of the prepolymer according to the present embodiment. For example, the lower cladding 20 may be prepared as a polymer sheet on the substrate 10 by coating the prepolymer on the substrate 10 and hardening the coated prepolymer. Or, a polymer sheet prepared by coating a blend of the prepolymer and a polymer on the substrate 10 and hardening the coated blend may be used as the lower cladding 20. For example, the polymer that may be blended with the prepolymer to form the lower cladding 20 may be a photocrosslinkable polymer, a thermocrosslinkable polymer, polyester, polyamide, polyimide, polycarbonate, polyethylene, polymethyl methacrylate, polypropylene or polyether. Or, a polymer sheet prepared by coating a blend of the prepolymer and a vinyl monomer on the substrate 10 and hardening the blend may be used as the lower cladding 20. The vinyl monomer that is miscible with the prepolymer used to prepare the lower cladding 20 is described with reference to the vinyl monomer used to prepare the substrate 10. Also, the lower cladding 20 may be a flexible polymer film formed of, for example, polyimide and poly(ethylene terephthalate) (PET).

Figure 1C:
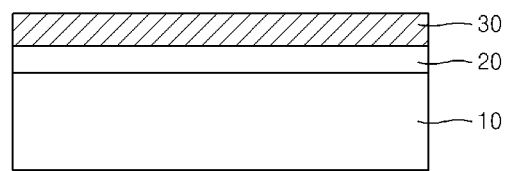

Referring to FIG. 1C, a core layer 30 is formed on the lower cladding 20.

The core layer 30 may be prepared as a polymer sheet by coating a compound represented by Formula 2 or 3 according to an embodiment of the present invention on the lower cladding 20 and hardening the compound. Also, a polymer sheet may be prepared by coating a blend of a prepolymer represented by Formula 2 or 3 according to an embodiment of the present invention and a polymer on the lower cladding 20 and hardening the compound. For example, the polymer that may be blended with the prepolymer to form the core layer 30 may be a photocrosslinkable polymer, a thermocrosslinkable polymer, polyester, polyamide, polyimide, polycarbonate, polyethylene, polymethyl methacrylate, polypropylene or polyether. Also, a polymer sheet may be prepared by coating a blend of the prepolymer of Formula 2 or 3 and a vinyl monomer on the lower cladding 20 and hardening the blend may be used as the core layer 30. The vinyl monomer that is miscible with the prepolymer used to prepare the core layer 30 is described with reference to the vinyl monomer used to prepare the substrate 10.

Figure 1D:
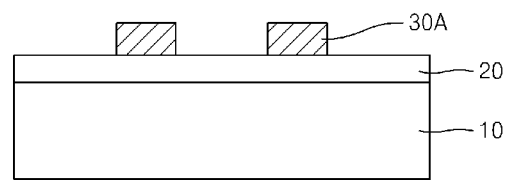

Referring to FIG. 1D, the core layer 30 is patterned using photolithography to form a plurality of cores 30A.

Alternatively, a core may be formed of metal instead of using the processes for forming the cores 30A shown in FIGS. 1C and 1D.

Figure 1E:
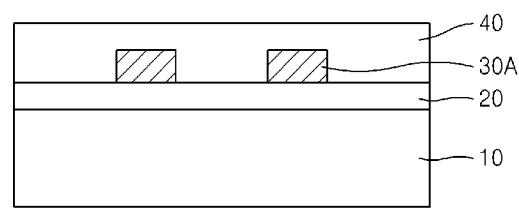

Referring to FIG. 1E, an upper cladding 40 is formed on the plurality of cores 30A.

The upper cladding 40 may be formed in the same manner as in the method of preparing the lower cladding 20 described with reference to FIG. 1B.

Figure 1F:
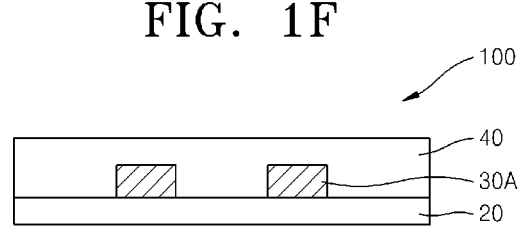

Referring to FIG. 1F, the substrate 10 is separated from the lower cladding 20 to prepare an optical waveguide 100 for optical interconnection according to the present embodiment.

If the prepolymer or the blend according to the present embodiment is used to form the substrate 10 as described above with reference to FIG. 1A, the process of forming the lower cladding 20 and the process shown in FIG. 1F may not be performed.

Even though not shown herein, in a process shown in FIG. 1E, a base film (not shown) may be formed on the upper cladding 40 using the compound or blend according to the present embodiment after forming the upper cladding 40.

In the optical waveguide 100 for optical interconnection prepared according to the process described with reference to FIGS. 1A to 1F, chemical structures of materials respectively forming the core layer 30, the lower cladding 20 and the upper cladding 40 may be selected such that the refractive index of the plurality of cores 30A is greater than that of the lower cladding 20 and the upper cladding 40 by about 0.001 to 0.5. Also, if a blend including the prepolymer is used, the blending ratio between the compounds forming each of the core layer 30, the lower cladding 20 and the upper cladding 40 may be controlled such that the refractive index of the plurality of cores 30A is greater than that of the lower cladding 20 and the upper cladding 40 by about 0.001 to 0.5.

FIGS. 2A to 2D are cross-sectional views of an optical waveguide 200 for optical interconnection according to another embodiment of the present invention, for describing a process for preparing the optical waveguide 200.

Reference numerals shown in FIGS. 2A to 2D denote the same elements shown in FIGS. 1A to 1F and descriptions thereof will not be repeated.

Figure 2A:
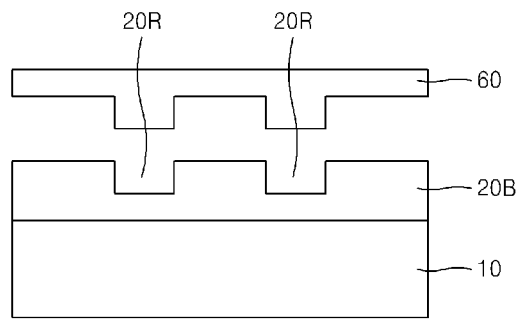
FIGS. 2A to 2D show cross-sectional views of an optical waveguide for optical interconnection at each fabrication step according to another embodiment of the present invention.

Referring to FIG. 2A, a lower cladding 20 is formed on a substrate 10 in the same manner as in FIGS. 1A and 1B, and a cladding pattern 20B having a plurality of recesses 20R is fabricated by applying an embossing process to the lower cladding 20 using a mold 60.

The embossing process may be conducted at a temperature greater than the glass transition temperature of the lower cladding 20, for example at a temperature ranging from 50 to 300° C.

Figure 2B:
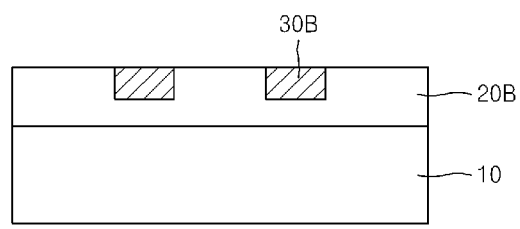

Referring to FIG. 2B, a core 30B is formed in the plurality of recesses 20R.

The core 30B may be formed in the same or similar manner like the core layer 30 described with reference to FIG. 1C.

Figure 2C:
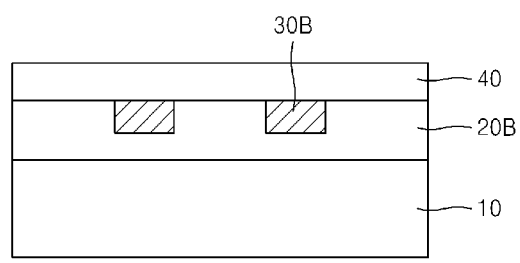

Referring to FIG. 2C, an upper cladding 40 is formed on the cladding pattern 20B and the core 30B.

The upper cladding 40 may be formed in the same manner like the upper cladding 40 described with reference to FIG. 1E.

Figure 2D:
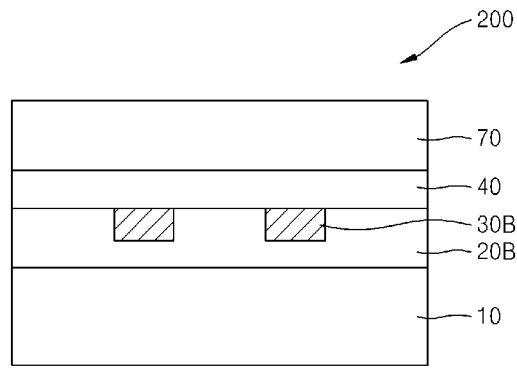

Referring to FIG. 2D, an upper base film 70 is formed on the upper cladding 40 to fabricate an optical waveguide for optical interconnection 200 according to the present embodiment.

The upper base film 70 may be a polymer film.

The process of forming the upper base film 70 described with reference to FIG. 2D may be omitted. In addition, if the substrate 10 is a silicon wafer, the substrate 10 may be separated in the optical waveguide for optical interconnection 200.

FIGS. 3A to 3D are cross-sectional views of an optical waveguide 300 for optical interconnection according to another embodiment of the present invention, for describing a process for preparing the optical waveguide for optical interconnection.

Reference numerals shown in FIGS. 3A to 3D denote the same elements shown in FIGS. 1A to 1F and descriptions thereof will not be repeated.

Figure 3A:
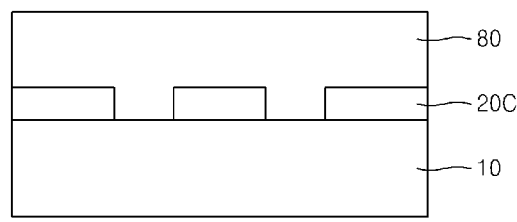
FIGS. 3A to 3D show cross-sectional views of an optical waveguide for optical interconnection at each fabrication step according to another embodiment of the present invention.

Referring to FIG. 3A, a lower cladding 20 is formed on a substrate 10 in the same manner as in FIGS. 1A and 1B. The compound represented by Formula 2 or 3 may be coated to form the lower cladding 20. Then, a cladding pattern 20C having a plurality of through-holes 20T is fabricated by applying an imprinting process to the lower cladding 20 using a mold 60, and simultaneously performing photocrosslinking or thermalcrosslinking.

If the imprinting process is performed as shown in FIG. 3A, a silicon wafer cannot be used as the substrate 10. In this regard, a polymer sheet prepared using the prepolymer or the blend may be used as the substrate 10.

Figure 3B:
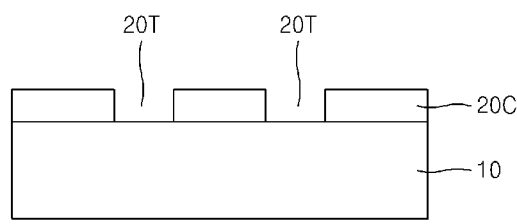

Referring to FIG. 3B, the mold 80 is removed.

Figure 3C:
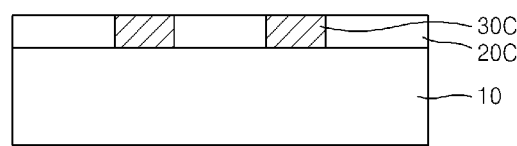

Referring to FIG. 3C, a core 30C is formed in the plurality of through-holes 20T.

The core 30C may be formed in the same or similar manner like the core layer 30 described with reference to FIG. 1C.

Figure 3D:
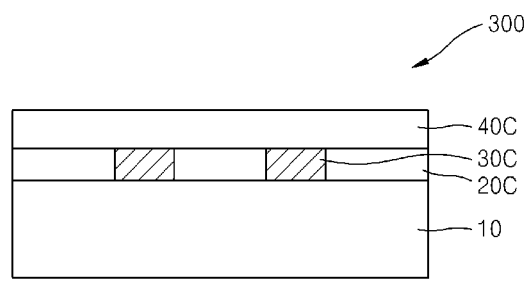

Referring to FIG. 3D, an upper cladding 40C is formed on the cladding pattern 20C and the core 30C to fabricate an optical waveguide for optical interconnection 300 according to the present embodiment.

The upper cladding 40C may be formed in the same manner like the upper cladding 40 described with reference to FIG. 1E.

Even though not shown herein, an upper base film 70 may further be formed on the upper cladding 40C as described with reference to FIG. 2D in the optical waveguide for optical interconnection 300.

The optical waveguides 100, 200, and 300 for optical interconnection according to embodiments of the present invention have been described herein with reference to FIGS. 1A to 1F, FIGS. 2A to 2D, and FIGS. 3A to 3D.

However, the present invention is not limited thereto, and an optical waveguide having a rib structure may also be used.

Figure 4:
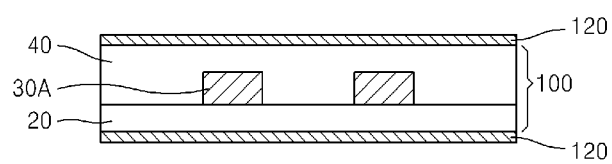
FIG. 4 is a cross-sectional view of the metal coated optical waveguide prepared from the optical waveguide shown in FIG. 1F.

FIG. 4 is a cross-sectional view of the optical waveguide 100 for optical interconnection shown in FIG. 1F when both surfaces thereof are coated with a metal sheet 120. The metal sheet 120 may be a copper thin film.

Figure 5:
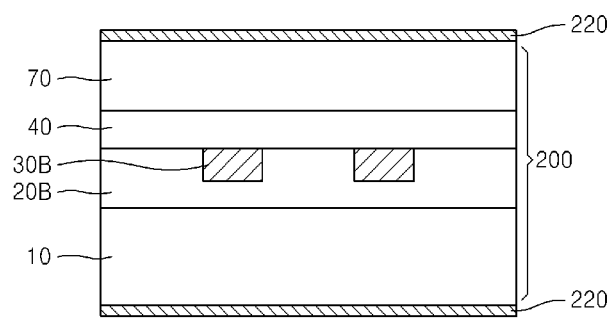
FIG. 5 is a cross-sectional view of the metal coated optical waveguide prepared from the optical waveguide shown in FIG. 2D.

FIG. 5 is a cross-sectional view of the optical waveguide 100 for optical interconnection shown in FIG. 2D when both surfaces thereof coated with a metal sheet 220. The metal sheet 220 may be a copper thin film.

Hereinafter, synthesis examples of the prepolymer and preparation examples of the polymer sheet and the optical waveguide will be described in more detail. However, it will be understood by those of ordinary skill in the art that various changes in form and details may be made therein without departing from the spirit and scope of the present invention, and these examples are not intended to limit the purpose and scope of the invention.

The order of the synthesis of the compound according to embodiments of the present invention is shown in Reaction Schemes 1 to 4.

An intermediate including a terminal hydroxyl moiety and a crosslinkable moiety is synthesized through Reaction Scheme 1 below.

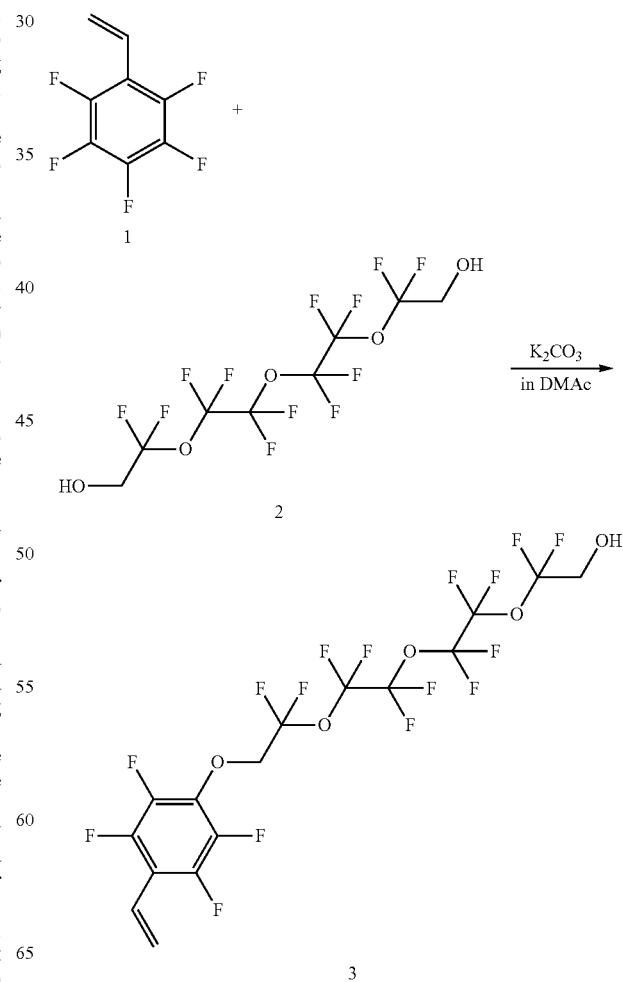

Reaction Scheme 1

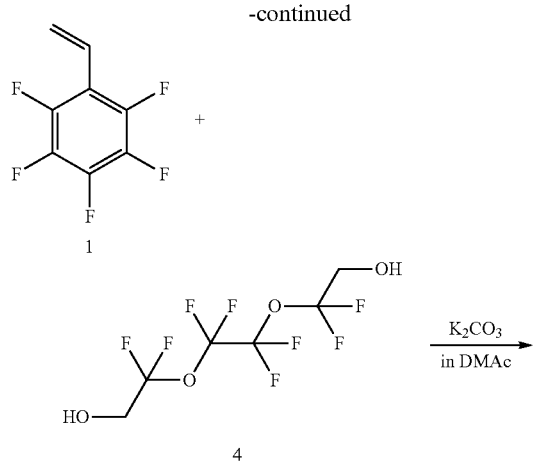
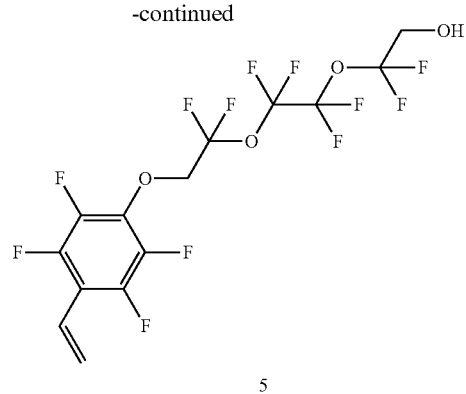
A decafluoro biphenyl derivative is synthesized through Reaction Scheme 2 below.
Reaction Scheme 2
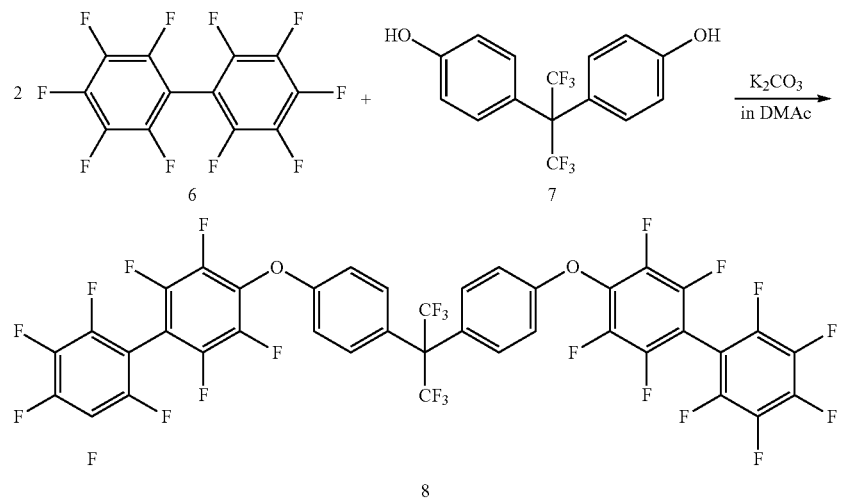
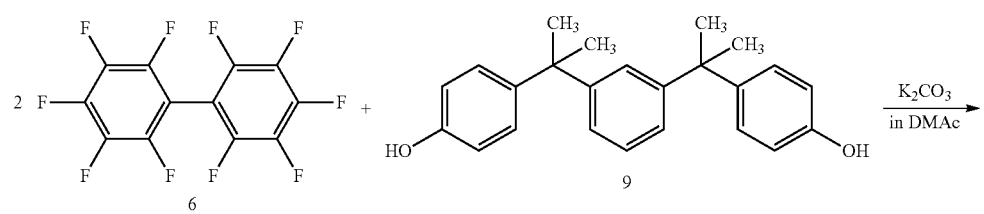
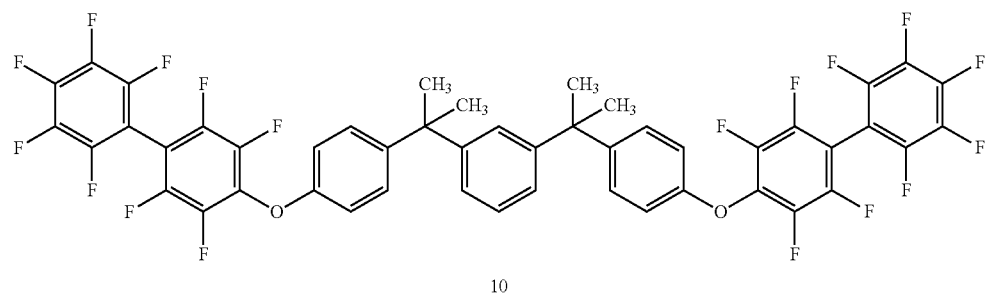

An imide type fluorinated aromatic moiety is synthesized through Reaction Scheme 3 below.
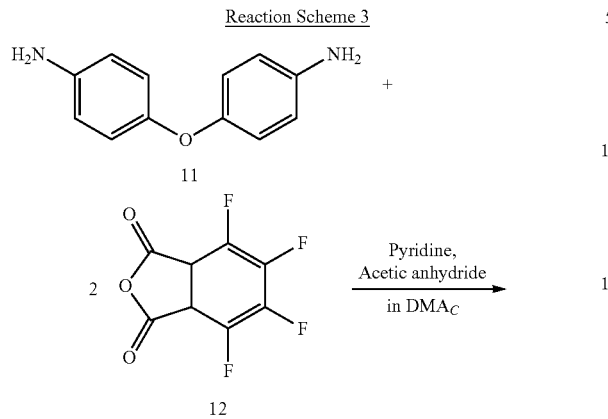
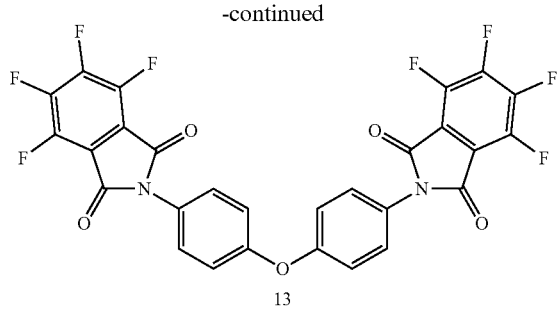
A curable ether-based liquid phase prepolymer is synthesized using decafluoro biphenyl through Reaction Scheme 4 below.
Reaction Scheme 4
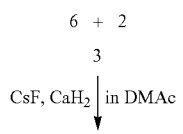
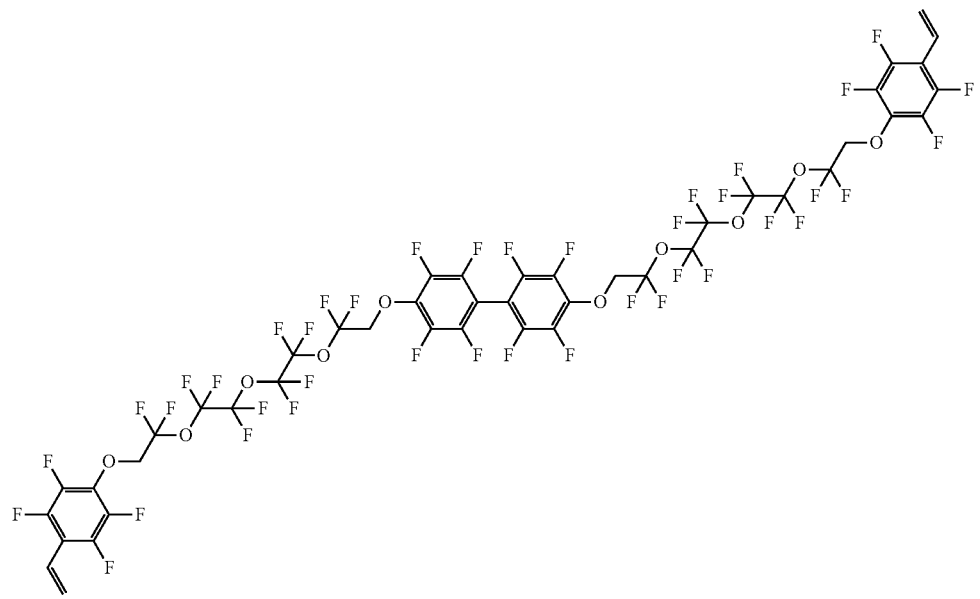
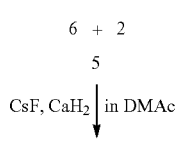

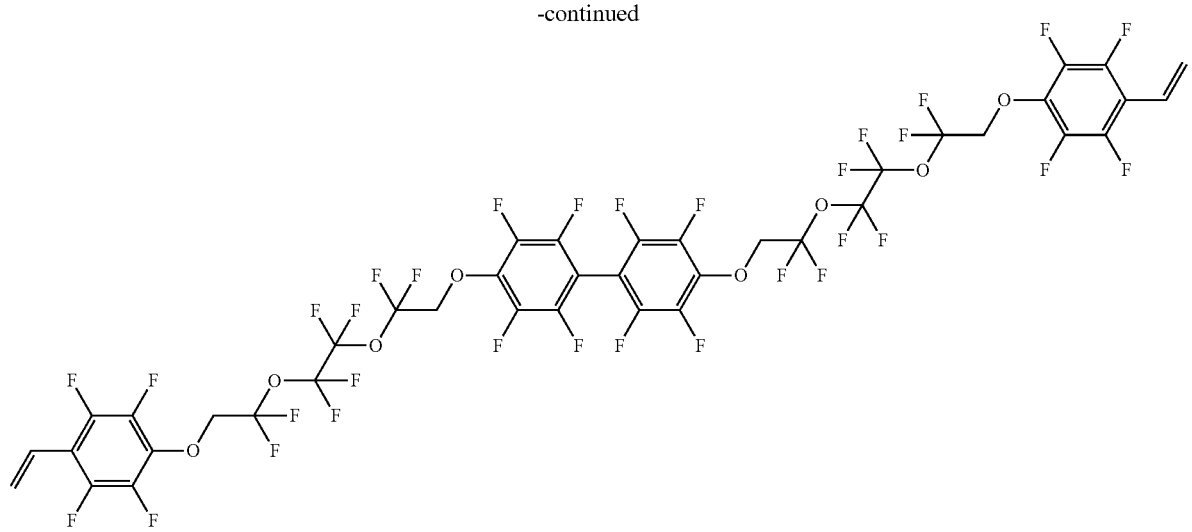
15
A curable ether-based liquid phase prepolymer is synthesized using a decafluoro biphenyl derivative through Reaction Scheme 5 below.

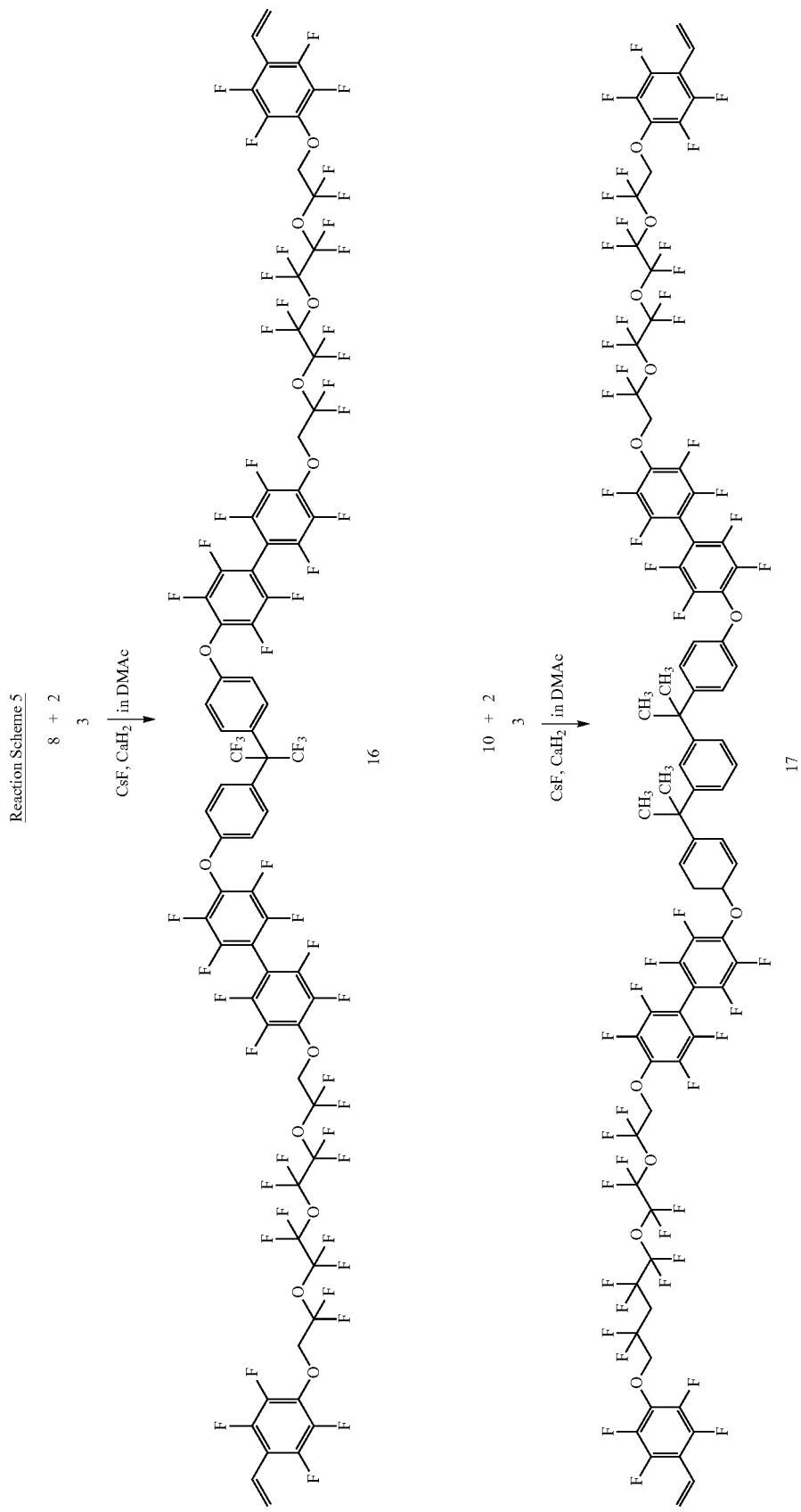

A curable etherimide-based liquid phase prepolymer is synthesized using imide type fluorinated aromatic moiety through Reaction Scheme 6 below.

Reaction Scheme 6
13 + 2 →₃ CsF, CaH₂ in DMAc
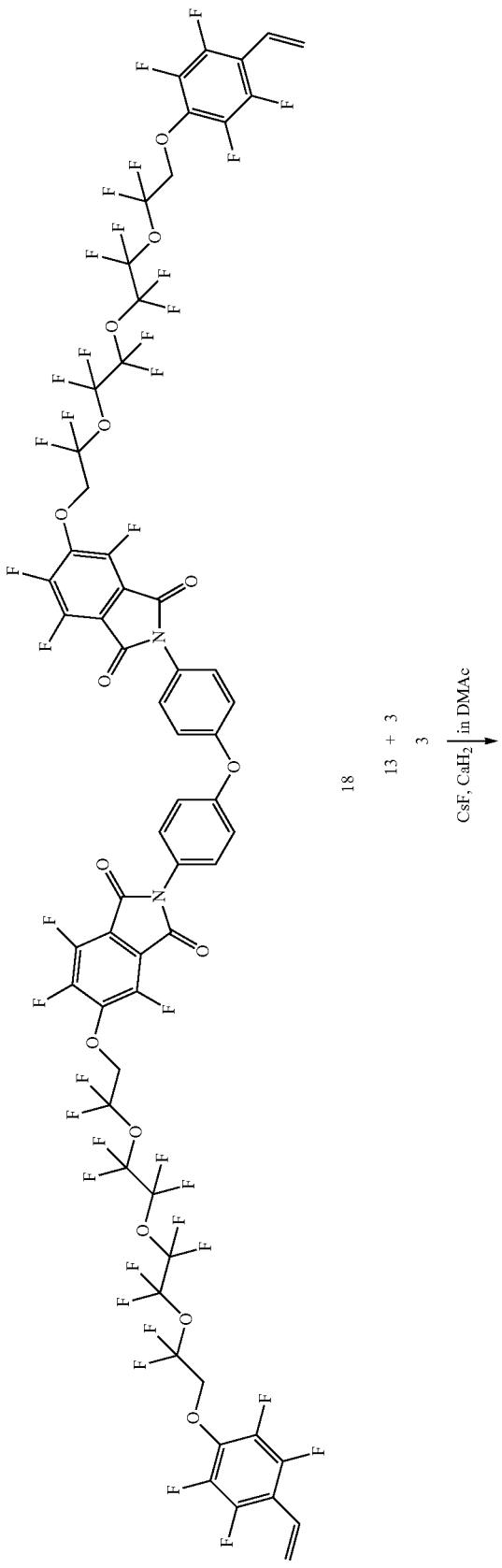
18
13 + 3 →₃ CsF, CaH₂ in DMAc

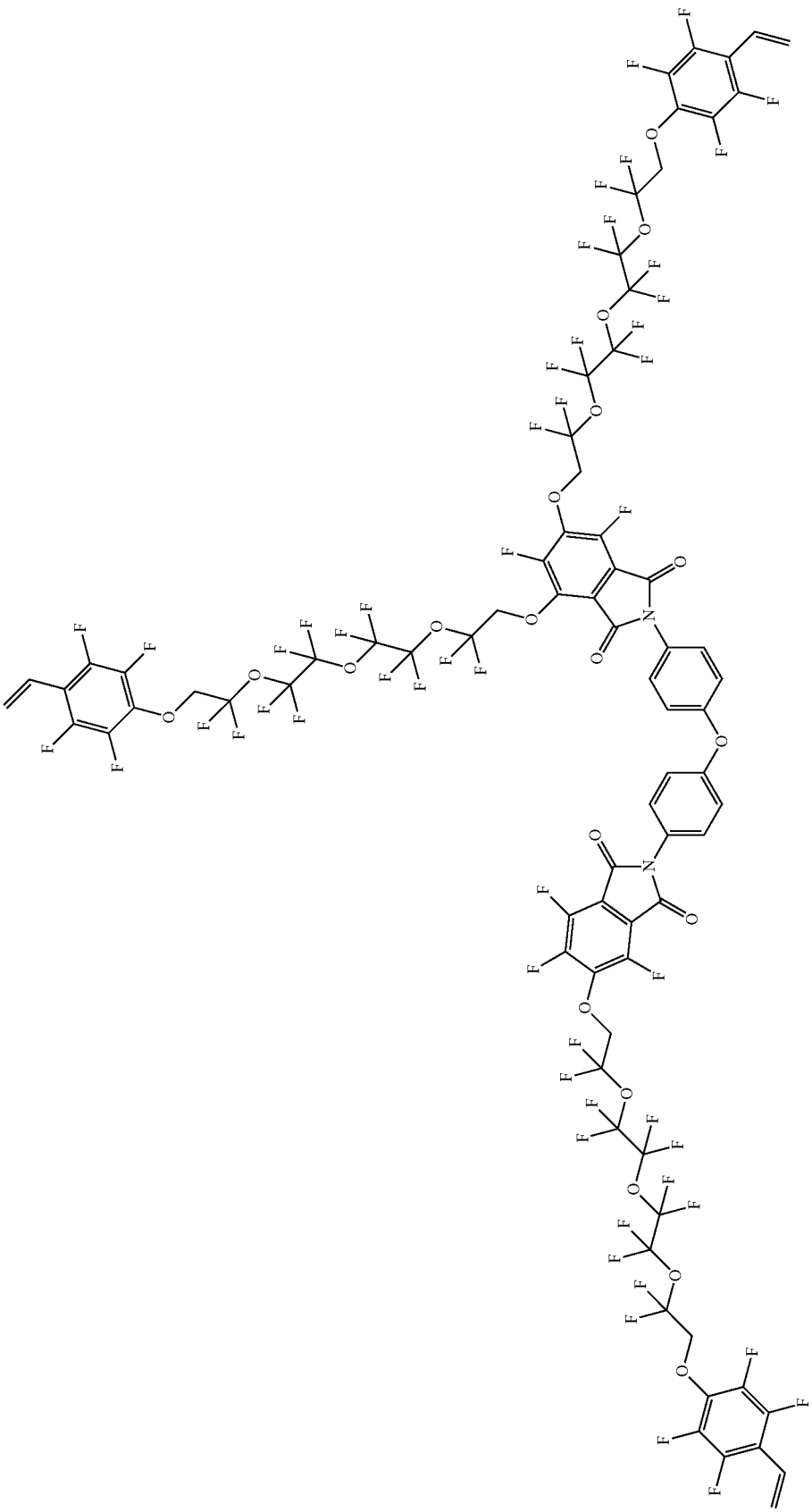

EXAMPLE 1

Synthesis of Compound 3 (2-(2-{2-[1,1-Difluoro-2-(2,3,5,6-tetrafluoro-4-vinyl-phenoxy)-ethoxy]-1,1,2,2-tetrafluoro-ethoxy}-1,1,2,2-tetrafluoro-ethoxy)-2,2-difluoro-ethanol)

20 g of (fluorinated tetraethylene)glycol [2] and 11.4 g of 2,3,4,5,6-pentafluorostyrene [1] were dissolved in 40 mL of anhydrous N,N'-dimethly acetamide (DMAc) in a 100 mL 2-neck flask under nitrogen, and 10.2 g of potassium carbonate was added thereto as a catalyst. The reaction was performed under nitrogen at a temperature ranging from 80 to 90° C. for about 24 hours. After the reaction was terminated, the reaction solution was cooled at room temperature and poured into distilled water. After the resultant was subjected to extraction using ethyl acetate, ethyl acetate was evaporated, and the resultant was dried in vacuum at 35° C. A brown resultant was purified by column chromatography using ethyl acetate/hexane (1/5, v/v) as an eluent to obtain a colorless transparent liquid product.

Yield: 12.78 g (45%); IR (KBr, cm$^{-1}$): 3383 (m, O—H str., hydroxyl); 3039 (w, =C—H str., vinyl); 2966 (w, C—H str., methylene); 1204, 1091 (s, C—O str., ether). $^1$H NMR (Chloroform-d$_1$, ppm): 6.69-6.59 (m, 1H, vinyl); 6.10-5.67 (m, 2H, vinyl); 4.53 (t, 2H, methylene); 3.94 (t, 2H, methylene); 2.74 (s, 1H, hydroxyl). $^{19}$F NMR (Chloroform-d$_1$, ppm): −79.29 (m, 2F); −81.74 (m, 2F); −89.76 (m, 8F); −145.28 (m, 2F); −159.11 (d, 2F).

EXAMPLE 2

Synthesis of Compound 5 (2-{2-[1,1-Difluoro-2-(2,3,5,6-tetrafluoro-4-vinyl-phenoxy)-ethoxy]-1,1,2,2-tetrafluoro-ethoxy}-2,2-difluoro-ethanol)

20 g of (fluorinated triethylene)glycol [4] and 13.2 g of 2,3,4,5,6-pentafluorostyrene [1] were dissolved in 40 mL of anhydrous N,N'-dimethly acetamide (DMAc) in a 100 mL 2-neck flask under nitrogen, and 14 g of potassium carbonate was added thereto as a catalyst. The reaction was performed under nitrogen at a temperature ranging from 80 to 90° C. for about 24 hours. After the reaction was terminated, the reaction solution was cooled at room temperature and poured into distilled water. After the resultant was subjected to extraction using ethyl acetate, ethyl acetate was evaporated, and the resultant was dried in a vacuum at 35° C. A brown resultant was purified by column chromatography using ethyl acetate/hexane (1/5, v/v) as an eluent to obtain a colorless transparent liquid product.

Yield: 13.52 g (42%); IR (KBr, cm$^{-1}$): 3374 (m, O—H str., hydroxyl); 3038 (w, =C—H str., vinyl); 2965 (w, C—H str., methylene); 1291, 1119 (s, C—O str., ether). $^1$H NMR (Chloroform-d$_1$, ppm): 6.69-6.59 (m, 1H, vinyl); 6.10-5.68 (m, 2H, vinyl); 4.53 (t, 2H, methylene); 3.96 (m, 2H, methylene); 2.74 (s, 1H, hydroxyl). $^{19}$F NMR (Chloroform-d$_1$, ppm): −78.70 (m, 2F); −80.95 (m, 2F); −89.08 (m, 4F); −144.45 (m, 2F); −158.17 (m, 2F).

EXAMPLE 3

Synthesis of Compound 8

10 g of decafluorobiphenyl (6) and 4.80 g of 2,2'-bis(4-hydroxyphenyl)hexafluoro propane (7) were dissolved in 28 mL of anhydrous N,N'-dimethly acetamide (DMAc) under nitrogen, and 6.0 g of potassium carbonate was added thereto as a catalyst. The reaction was performed under nitrogen at a temperature ranging from 80 to 90° C. for about 24 hours. After the reaction was terminated, the reaction solution was cooled at room temperature, poured into distilled water, washed, and dried under vacuum at 80° C.

Yield: 10.70 g (77.8%);IR (KBr, cm$^{-1}$): 3056 (w, =C—H str., aromatic); 1608, 1531 (m, C=C str., aromatic); 1178, 1076 (s, C—O str., ether). $^1$H NMR (Chloroform-d$_1$, ppm): 7.46-7.07 (m, 8H, aromatic). $^{19}$F NMR (Chloroform-d$_1$, ppm): −64.11 (s, 6F); −137.39 (m, 4F); −137.58 (m, 4F); −149.90 (m, 2F); −152.43 (m, 4F); −160.38 (m, 4F).

EXAMPLE 4

Synthesis of Compound 10

10 g of Compound 6 and 4.94 g of 1,3-bis[2-(4-hydroxyphenyl)-2-propyl]benzene (9) were dissolved in 35 mL of anhydrous N,N'-dimethly acetamide (DMAc) under nitrogen and 6.0 g of potassium carbonate was added thereto as a catalyst. The reaction was performed under nitrogen at a temperature ranging from 80 to 90° C. for about 24 hours. After the reaction was terminated, the reaction solution was cooled at room temperature, poured into a mixture of methanol and distilled water (1/1, v/v), washed, and dried under vacuum at 80° C.

Yield: 8.84 g (63.6%);(KBr, cm$^{-1}$): 3041 (w, =C—H str., aromatic); 2971 (m, C—H str., methyl); 1604, 1530 (m, C=C str., aromatic); 1209, 1073 (s, C—O str., ether).$^1$H NMR (Chloroform-d$_1$, ppm): 7.43-7.15 (m, 12H, aromatic); 1.88 (s, 12H, methyl). $^{19}$F NMR (Chloroform-d$_1$, ppm): −138.38 (m, 8F); −150.04 (m, 2F); −152.95 (m, 4F); −160.59 (m, 4F).

EXAMPLE 5

Synthesis of Compound 13

4 g of oxydianiline (11) was completely dissolved in 30 mL of DMAc in a 100 mL 2-neck flask under nitrogen, and 10 g of anhydrous tetrafluorophthalic anhydride (12) was added thereto. The reaction was performed at room temperature for about 4 hours. Then, 4.8 mL of pyridine and 5.6 mL of anhydrous acetic acid were added thereto, and the reaction was further conducted for 24 hours for imidization. The resultant was poured into distilled water to obtain a yellow precipitate, and the yellow precipitate was dried in vacuum at 70° C. The resultant was purified by column chromatography using ethyl acetate as an eluent.

Yield: 5.22 g (41%); m. p.: 348-349° C.; IR (KBr, cm$^{-1}$): 3115 (w, =C—H str., aromatic); 1785 (m, C=O str., imide); 1258, 1084 (s, C—O str., ether). $^1$H NMR (dmso-d$_6$, ppm): 7.51-7.26 (m, 8H, aromatic).

EXAMPLE 6

Synthesis of Compound 14 (2,3,5,6,2',3',5',6'-octafluoro-4,4'-bis-[2-(2-{2-[1,1-Difluoro-2-(2,3,5,6-tetrafluoro-4-vinyl-phenoxy)-ethoxy]-1,1,2,2-tetrafluoro-ethoxy}-1,1,2,2-tetrafluoro-ethoxy)-2,2-difluoro-ethoxy]-biphenyl)

1.50 g of Compound 6 and 5.25 g of Compound 3 were completely dissolved in 15 mL of DMAc in a 50 mL 2-neck flask under nitrogen, and 0.07 g of cesium fluoride and 0.57 g of calcium hydride were added thereto as catalysts. The reaction was performed at 60° C. for about 2 days. After the reaction was terminated, the reaction solution was poured into distilled water, subjected to extraction using ethyl acetate, and dried under vacuum at 35° C. The resultant was purified by column chromatography using ethyl acetate/hexane (1/5, v/v) as an eluent, the eluent was completely removed under reduced pressure, and the resultant was dried under vacuum at 35° C. to obtain a colorless transparent liquid product with high viscosity.

Yield: 4.01 g (61%). IR (KBr, cm$^{-1}$): 3039 (w, =C—H str., vinyl); 2971 (w, C—H str., methylene); 1210, 1085 (s, C—O str., ether). $^1$H NMR (Chloroform-d$_1$, ppm): 6.69-6.56 (m, 2H, vinyl); 6.10-5.67 (m, 4H, vinyl); 4.64 (t, 4H, methylene); 4.53 (t, 4H, methylene). $^{19}$F NMR (Chloroform-d$_1$, ppm): −79.29 (m, 8F); −89.54 (m, 16F); −139.26 (m, 4F); −145.01 (m, 4F); −156.49 (d, 4F); −158.79 (m, 4F).

EXAMPLE 7

Synthesis of Compound 15

1.50 g of Compound 6 and 4.30 g of Compound 5 were completely dissolved in 10 mL of DMAc in a 50 mL 2-neck flask under nitrogen, and 0.07 g of cesium fluoride and 0.57 g of calcium hydride were added thereto as catalysts. The reaction was performed at 60° C. for about 2 days. After the reaction was terminated, the reaction solution was poured into distilled water, subjected to extraction using ethyl acetate, and dried under vacuum at 35° C. The resultant was purified by column chromatography using ethyl acetate/hexane (1/5, v/v) as an eluent, the eluent was completely removed under reduced pressure, and the resultant was dried under vacuum at 35° C. to obtain a colorless transparent liquid product with high viscosity.

Yield: 4.93 g (89%). IR (KBr, cm$^{-1}$): 3038 (w, =C—H str., vinyl); 2971 (w, C—H str., methylene); 1297, 1119 (s, C—O str., ether). $^1$H NMR (Chloroform-d$_1$, ppm): 6.63-6.53 (m, 2H, vinyl); 6.05-5.33 (m, 4H, vinyl); 4.59 (t, 4H, methylene); 4.46 (m, 4H, methylene). $^{19}$F NMR (Chloroform-d$_1$, ppm): −78.81 (m, 8F); −89.17 (m, 8F); −138.81 (m, 4F); −144.56 (m, 4F); −155.90 (d, 4F); −158.21 (m, 4F).

EXAMPLE 8

Synthesis of Compound 16

3.93 g of Compound 8 and 4.75 g of Compound 3 were completely dissolved in 25 mL of DMAc under nitrogen, and 0.06 g of cesium fluoride and 0.52 g of calcium hydride were added thereto as catalysts. The reaction was performed at 60° C. for about 2 days. After the reaction was terminated, the reaction solution was poured into distilled water, subjected to extraction using ethyl acetate, and dried under vacuum at 35° C. The resultant was purified by column chromatography using ethyl acetate/hexane (1/5, v/v) as an eluent, the eluent was completely removed under reduced pressure, and the resultant was dried under vacuum at 35° C. to obtain a colorless transparent liquid product with high viscosity.

Yield: 7.33 g (86%). IR (KBr, cm$^{-1}$): 3053 (w, =C—H str., vinyl); 2970 (w, C—H str., methyl); 1609, 1507 (m, C=C str., aromatic); 1178, 1074 (s, C—O str., ether). $^1$H NMR (Chloroform-d$_1$, ppm): 7.46-7.06 (m, 8H, aromatic); 6.69-5.67 (m, 6H, vinyl); 4.67-4.50 (m, 8H, methylene). $^{19}$F NMR (Chloroform-d$_1$, ppm): −64.24 (d, 6F); −78.60 (m, 8F); 88.83 (m, 16F); 138.31 (m, 8F); 144.30 (m, 4F); 152.79 (d, 4F) 4F); 155.57 (d, 4F); 158.05 (m, 4F).

EXAMPLE 9

Synthesis of Compound 17

4.0 g of Compound 10 and 4.92 g of Compound 3 were completely dissolved in 30 mL of DMAc under nitrogen, and 0.06 g of cesium fluoride and 0.52 g of calcium hydride were added thereto as catalysts. The reaction was performed at 60° C. for about 2 days. After the reaction was terminated, the reaction solution was poured into distilled water, subjected to extraction using ethyl acetate, and dried under vacuum at 35° C. The resultant was purified by column chromatography using ethyl acetate/hexane (1/5, v/v) as an eluent, the eluent was completely removed under reduced pressure, and the resultant was dried under vacuum at 35° C. to obtain a colorless transparent liquid product with high viscosity.

Yield: 7.72 g (89%).IR (KBr, cm$^{-1}$): 3038 (w, =C—H str., vinyl); 2972 (w, C—H str., methyl); 1604, 1540 (m, C=C str., aromatic); 1209, 1115 (s, C—O str., ether). $^1$H NMR (Chloroform-d$_1$, ppm): 7.10-6.82 (m, 12H, aromatic); 6.58-5.56 (m, 6H, vinyl); 4.53-4.40 (m, 8H, methylene). $^{19}$F NMR (Chloroform-d$_1$, ppm): −78.46 (m, 8F); −88.74 (m, 16F); −138.44 (m, 8F); −144.15 (m, 4F); −153.24 (m, 4F); 155.68 (m, 4F); 157.95 (m, 4F).

EXAMPLE 10

Synthesis of Compound 18

0.80 g of Compound 13 and 1.58 g of Compound 3 were completely dissolved in 13 mL of DMAc in a 50 mL 2-neck flask under nitrogen, and 0.02 g of cesium fluoride and 0.17 g of calcium hydride were added thereto as catalysts. The reaction was performed at 60° C. for about 2 days. After the reaction was terminated, the reaction solution was poured into distilled water, subjected to extraction using ethyl acetate, and dried under vacuum at 35° C. The resultant was purified by column chromatography using ethyl acetate/hexane (1/5, v/v) as an eluent, the eluent was completely removed under reduced pressure, and the resultant was dried under vacuum at 35° C. to obtain a light yellow transparent liquid product with high viscosity.

Yield: 1.93 g (84%). IR (KBr, cm$^{-1}$): 3051 (w, =C—H str., vinyl); 2971 (w, C—H str., methylene); 1782 (m, C=O str., imide); 1293, 1115 (s, C—O str., ether). $^1$H NMR (dmso-d$_6$, ppm): 7.50-7.25 (m, 8H, aromatic); 6.70-6.58 (m, 2H, vinyl); 6.03-5.74 (m, 4H, vinyl); 5.14 (t, 4H, methylene); 5.02-4.91 (m, 4H, methylene). $^{19}$F NMR (dmso-d$_6$, ppm): −77.87 (m, 8F); −88.41 (m, 16F); −133.45 (m, 6F); −145.22 (m, 4F); −157.46 (m, 4F).

EXAMPLE 11

Synthesis of Compound 19

1.50 g of Compound 13 and 4.49 g of Compound 3 were completely dissolved in 13 mL of DMAc in a 50 mL 2-neck flask under nitrogen, and 0.06 g of cesium fluoride and 0.47 g of calcium hydride were added thereto as catalysts. The reaction was performed at 60° C. for about 2 days. After the reaction was terminated, the reaction solution was poured into distilled water, subjected to extraction using ethyl acetate, and dried under vacuum at 35° C. The resultant was purified by column chromatography using ethyl acetate/hexane (1/1, v/v) as an eluent, the eluent was completely removed under reduced pressure, and the resultant was dried under vacuum at 35° C. to obtain a light yellow transparent liquid product with high viscosity.

Yield: 4.72 g (83%). IR (KBr, cm$^{-1}$): 3038 (w, =C—H str., vinyl); 2972 (w, C—H str., methylene); 1780 (m, C=O str., imide); 1293, 1114 (s, C—O str., ether). $^1$H NMR (dmso-d$_6$, ppm): 7.48-7.25 (m, 7H, aromatic); 6.68-6.41 (m, 3H, vinyl); 6.02-5.69 (m, 6H, vinyl); 4.95 (m, 6H, methylene); 4.71 (m, 6H, methylene). $^{19}$F NMR (dmso-d$_6$, ppm): −77.86 (m, 12F); −88.26 (m, 24F); −133.13 (m, 5F); −145.22 (m, 6F); −157.47 (d, 6F).

EXAMPLE 12

Preparation of Flexible Thick Film Polymer Sheet

Each of 1.0 g of the ether-based liquid phase prepolymer formed of Compound 14 synthesized according to Example 6, 1.0 g of the ether-based liquid phase prepolymer formed of Compound 15 synthesized according to Example 7, a mixture of 0.8 g of the ether-based liquid phase prepolymer formed of Compound 16 synthesized according to Example 8 and 0.2 g of 2,3,4,5,6-pentafluoro styrene, and a mixture of 0.85 g of the ether-based liquid phase prepolymer formed of Compound 17 synthesized according to Example 9 and 0.15 g of methyl methacrylate, was mixed with 1.5 wt % of CGI 124 photo-curable initiator to prepare solutions for optical waveguides. Then, micro particles were completely removed by filtering the solutions using a 0.2 μm filter, and each of the filtrates was spin coated on a silicon wafer at 800 rpm for 20 seconds, exposed to UV for 10 minutes, and post-treated at about 150° C. under nitrogen. The obtained films were separated from the silicon wafer to obtain polymer sheets having a thickness of about 40 μm.

EXAMPLE 13

Measuring Thermal and Mechanical Properties of Polymer Sheet 1.0 g of the ether-based liquid phase prepolymer formed of Compound 14 synthesized according to Example 6 (Sample 1), 1.0 g of the ether-based liquid phase prepolymer formed of Compound 15 synthesized according to Example 7 (Sample 2), a mixture of 0.8 g of the ether-based liquid phase prepolymer formed of Compound 16 synthesized according to Example 8 and 0.2 g of 2,3,4,5,6-pentafluoro styrene (Sample 3), a mixture of 0.85 g of the ether-based liquid phase prepolymer formed of Compound 17 synthesized according to Example 9 and 0.15 g of methyl methacrylate (Sample 4), and a mixture of 0.85 g of the ether-based liquid phase prepolymer formed of Compound 17 synthesized according to Example 9 and 0.11 g of N-propylmaleimide (Sample 5) were prepared. Each of Samples 1 to 5 was mixed with 1.5 wt % of CGI 124 photo-curable initiator to prepare solutions for optical waveguides. Each of the solutions was spin coated on a glass plate, exposed to UV, and heat-treated. Then, the glass plate was removed to prepare polymer sheets obtained from Samples 1 to 5.

Figure 6:
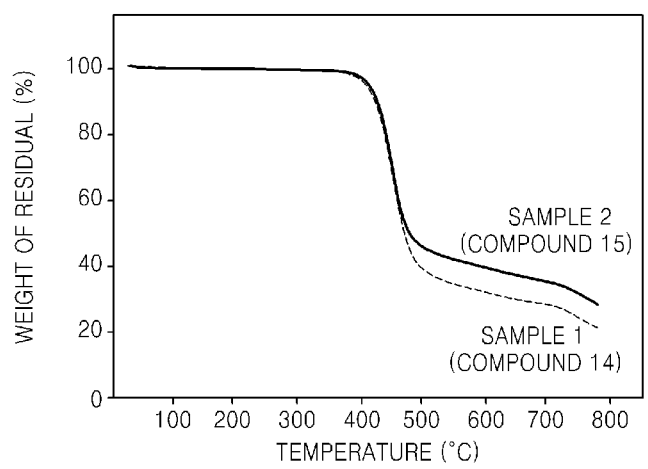
FIG. 6 is a graph illustrating the results of thermogravimetric analysis of polymer sheets according to an embodiment of the present invention.

FIG. 6 is a graph illustrating the results of thermogravimetric analysis of the polymer sheets of Sample 1 from Compound 14 and Sample 2 from Compound 15.

Referring to FIG. 6, the polymer sheets of Samples 1 and 2 have thermal stability up to 415° C.

Table 1 shows tensile strengths of the polymer sheets of Samples 3 to 5.

TABLE 1

| Samples | Maximum tensile strength (MPa) | Strain at break (%) | Initial modulus (Gpa) |
|---|---|---|---|
| Sample 3 | 34.8 | 4.6 | 1.06 |
| Sample 4 | 33.6 | 3.4 | 1.13 |
| Sample 5 | 43.5 | 4.7 | 1.30 |

Referring to Table 1, the polymer sheets of Samples 3 to 5 respectively have maximum tensile strengths of 34.8 Mpa, 33.6 MPa, and 43.5 Mpa, and initial moduli of 1.06 Gpa, 1.13 Gpa, and 1.30 GPa. Thus, it can be seen that the polymer sheets of Samples 3 to 5 have excellent mechanical characteristics. In particular, N-propylmaleimide contained in Sample 5 alternatively reacts with styrene so as to act as a chain extender of the prepolymer having styrene at one end thereof.

EXAMPLE 14

Preparing Polymer Optical Waveguide and Measuring Propagation Loss

A core layer of an optical waveguide is prepared using each of the ether-based liquid phase prepolymer formed of Compound 14 synthesized according to Example 6 and the ether-based liquid phase prepolymer formed of Compound 15 synthesized according to Example 7. A cladding layer is formed on the upper and lower surfaces of the core layer using LFR 383 (refractive index: 1.39, Chemoptics, Inc.).

The thicknesses of the upper and lower cladding layers formed on the silicon wafer were respectively 30 μm, and the optical waveguide core had a rib structure with a thickness of 30 μm and an etching depth of 3 μm. Samples were prepared such that straight optical waveguides of the rib structure have the sizes of 1.5 cm, 2.5 cm, 3.5 cm, 4.5 cm and 5.5 cm to measure the propagation loss. The propagation loss of the optical waveguide was measured using a cutback method. Insertion loss of each of the samples having different propagation lengths was measured, and the results were fitted to measure propagation loss. The insertion loss was measured using an autoaligner in a transverse electric (TE)-mode and a traverse magnetic (TM)-mode at a wavelength of 1.31 μm.

The refractive indices of the films obtained using Compounds 14 and 15 for TE- and TM-polarized light at a wavelength of 1.31 μm were 1.4169 and 1.4168 (Compound 14) and 1.4366 and 1.4366 (Compound 15), respectively.

Figure 7:
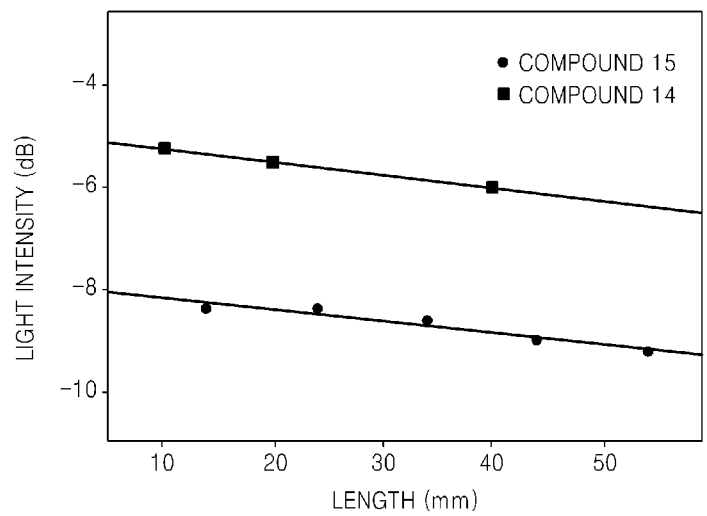
FIG. 7 is a graph illustrating insertion loss according to the length of a core of an optical waveguide according to an embodiment of the present invention.

FIG. 7 is a graph illustrating insertion loss according to the propagation lengths of the optical waveguide cores respectively obtained using Compounds 14 and 15. The optical propagation loss of the optical waveguide obtained using Compound 14 was about 0.23 dB/cm and the optical propagation loss of the optical waveguide obtained using Compound 15 was about 0.25 dB/cm, respectively, for TE-polarized light at a wavelength of 1.31 μm.

EXAMPLE 15

Preparing Flexible Polymer Optical Waveguide and Measuring Variation of Optical Loss with Bending Radii Flexible optical waveguides including an upper and lower claddings formed of the ether-based liquid phase prepolymer formed of Compound 14 synthesized according to Example 6, and a core layer formed of the ether-based liquid phase prepolymer formed of Compound 15 synthesized according to Example 7, were prepared. In more particular, Compound 14 including a photocrosslinkable agent was spin coated on a metal thin film formed on a silicon wafer and photocrosslinked to form the lower cladding layer. Then, Compound 15 including a photocrosslinkable agent was spin coated thereon, patterned by photocroslinking using a mask, and developed to form the core. Then, Compound 14 including a photocrosslinkable agent was spin coated and photocrosslinked to form the upper cladding layer. The obtained flexible polymer optical waveguide sheet had a thickness of about 25 μm and the core had a channel structure with a width of 9 μm and a height of 5 μm.

A single- and multi-mode optical fibers were connected to each of the ends of the core in order to measure propagation loss according to the bending radii of the optical waveguide sheet.

Figure 8:
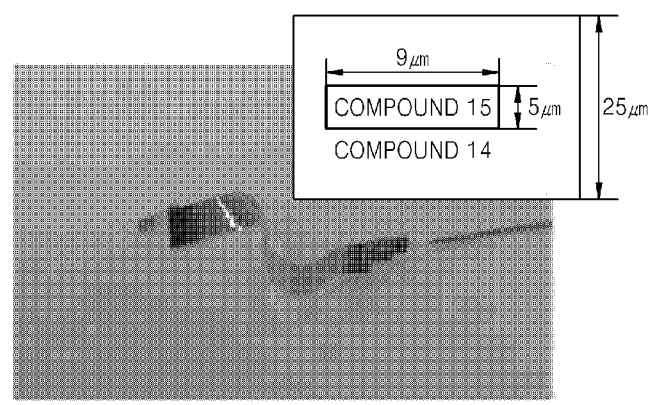
FIG. 8 is a photograph of an optical waveguide for optical interconnection according to an embodiment of the present invention.

FIG. 8 is a photograph of an optical waveguide sheet including single- and multi-mode optical fibers at each of ends thereof and an optical waveguide.

Figure 9:
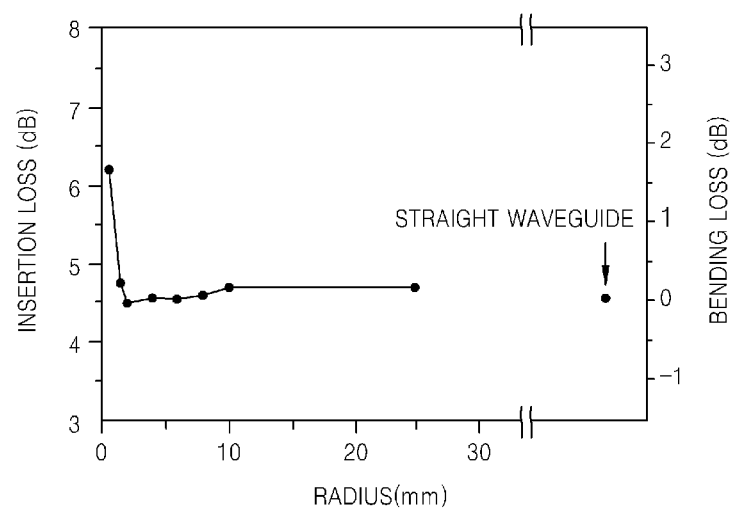
FIG. 9 is a graph illustrating variation of the optical propagation loss with the bending radii of an optical waveguide for optical interconnection according to an embodiment of the present invention.

FIG. 9 is a graph illustrating the variation of optical propagation loss (insertion loss) of the optical waveguide with the bending radii of the optical waveguide sheet.

Referring FIG. 9, no optical propagation loss was observed until the radius reached 1.5 mm.

A crosslinkable moiety is chemically bound to one end of the compound according to the present invention, and the compound includes aromatic and aliphatic moieties and a large amount of fluorine. If the prepolymer according to the present invention is a liquid type prepolymer having a molecular weight greater than 1000, a solvent is not required in the coating process for forming a film or a sheet using the prepolymer. If the prepolymer is a solid type prepolymer having a molecular weight greater than 1000, it is easily dissolved in a vinyl monomer, so that a solvent is not required in the coating process. In addition, the liquid type prepolymer having a high viscosity may be efficiently used to prepare a thick film. The viscosity and refractive index of the liquid type prepolymer may vary according to the molecular weight and the chemical structure of the prepolymer. In addition, the viscosity and refractive index of the blend may vary according to the mixing ratio of the prepolymer and the vinyl monomer. Due to a high molecular weight, the prepolymer may form a film having a high molecular weight after thermalcrosslinking or photocrosslinking. Since the prepolymer may include aromatic moieties, mechanical properties of the thick film such as tensile strength, abrasion resistance, fatigue resistance, and bending strength may be improved after the thick film is formed of the prepolymer or the blend according to the present invention. In addition, since the imide type prepolymer that is crosslinkable in a three-dimensional space may further improve mechanical properties of the thick film. Since the prepolymer or the blend has a large amount of fluorine, optical loss may be reduced using the compound or the blend as a material for the optical waveguide. In addition, by physically or chemically mixing prepolymers having different structures, optical and mechanical characteristics may be controlled. According to the present invention, a thick film polymer sheet having a thickness of several tens or more μm and excellent mechanical characteristics and low optical loss may be prepared. By using the polymer sheet, the optical waveguide may be efficiently prepared. The optical waveguide has low optical loss, excellent thermal stability, excellent chemical resistance, and excellent mechanical properties such as tensile strength, abrasion resistance, fatigue resistance, and bending strength. Thus, the shape of the optical waveguide may be maintained without a substrate, and flexibility thereof may be maintained for a long period of time. In addition, due to the excellent fatigue resistance, the optical waveguide may be used for a long period of time. Since each of the core and the cladding of the optical waveguide for optical interconnection has excellent mechanical properties, metal such as copper may be directly coated between and on the upper and lower surfaces of the cladding of the optical waveguide for optical interconnection, and the metal may be used an electric circuit. Thus, a flexible copper-clad waveguide laminate (FCCWL) and the related printed circuit board (PCB) by which optical and electric signals may be simultaneously transferred may be prepared.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A blend prepared by mixing a prepolymer and a vinyl monomer,
   wherein the prepolymer is prepared by a condensation reaction between a first compound represented by Formula (1) below:

Ar—H  (1), where Ar comprises (a) a crosslinkable moiety at one end, (b) a moiety selected from the group consisting of —O—, —S—, —COO—, —CO—, —COS—, —SO$_2$—, and —NH—, and (c) one or two repeating units selected from the group consisting of:

where A is carbon or nitrogen, and X is hydrogen or halogen; and
   a second compound selected from the group consisting of an aromatic moiety having a structure as follows:

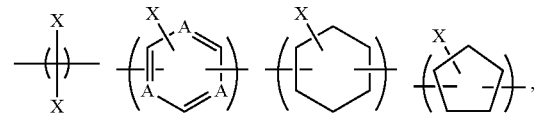

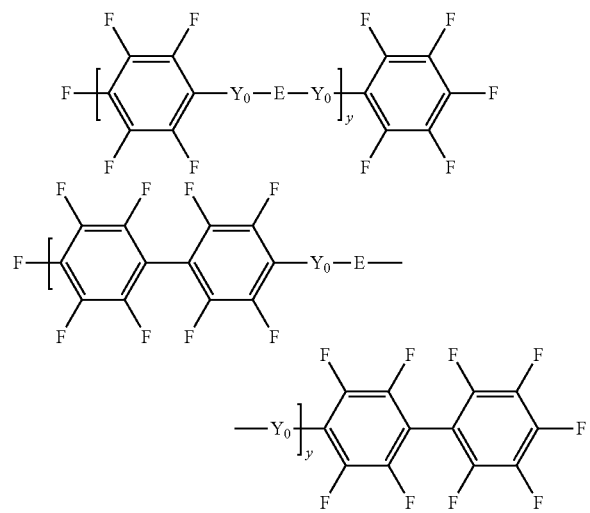

-continued

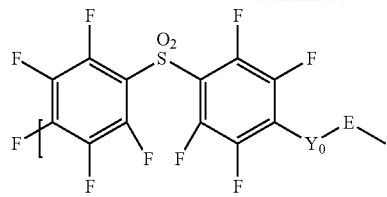

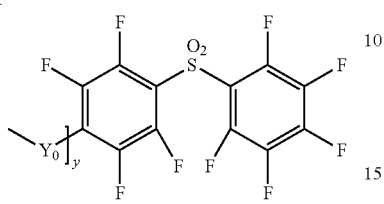

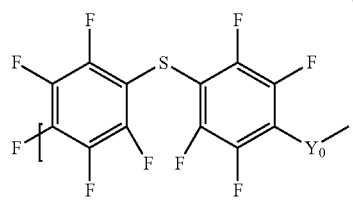

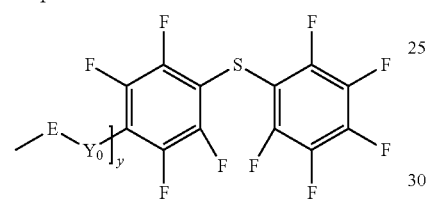

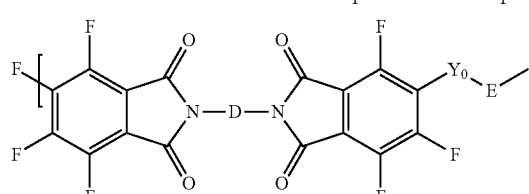

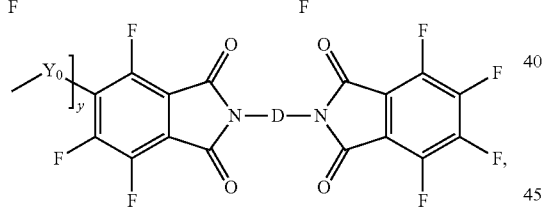

where y is an integer from 0 to 1000, $Y_0$ is selected from the group consisting of —, —O—, —S—, —COO—, —CO—, —COS—, —SO$_2$— and —NH—, E is selected from the group consisting of structures as follows:

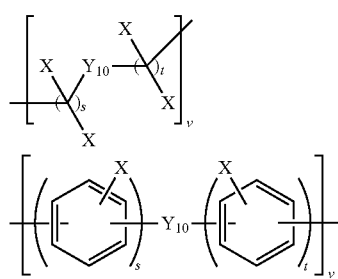

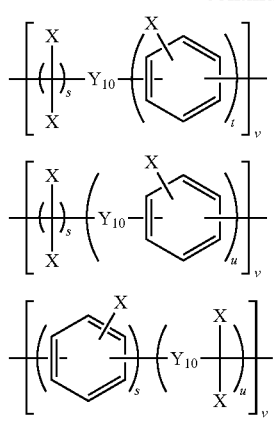

where $Y_{10}$ is selected from the group consisting of —, —O—, —S—, —COO—, —CO—, —COS—, —SO$_2$— and —NH—, s and t are each independently an integer from 1 to 50, u is an integer from 0 to 50, and v is an integer from 1 to 100, and D is selected from the group consisting of structures as follows:

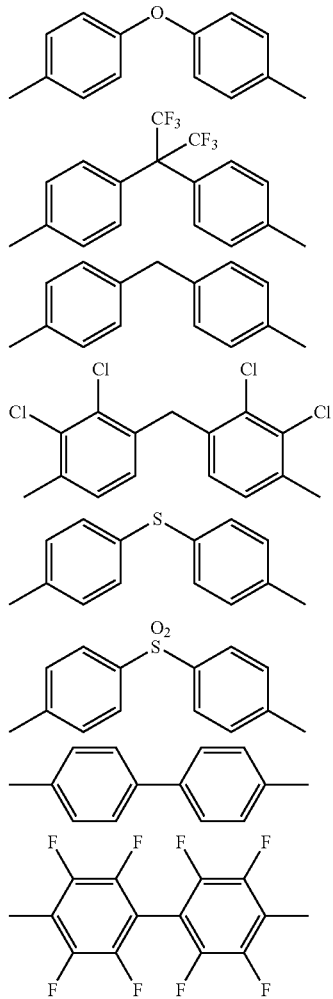

-continued

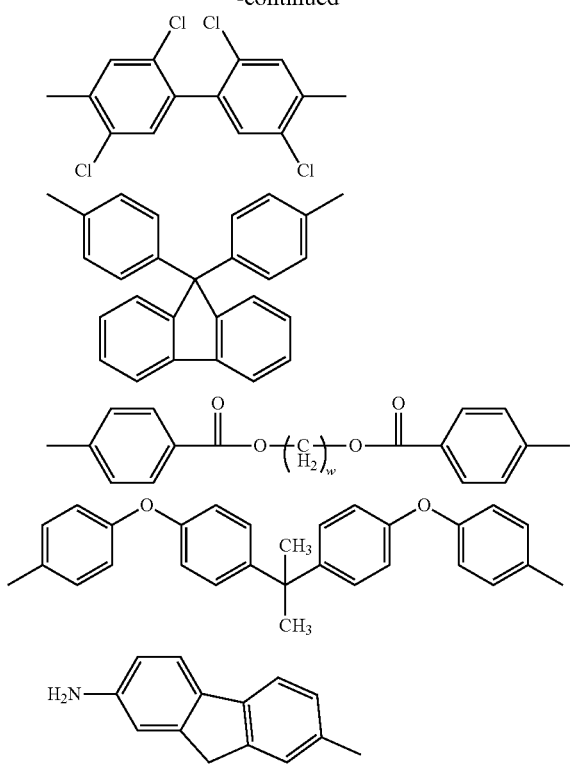

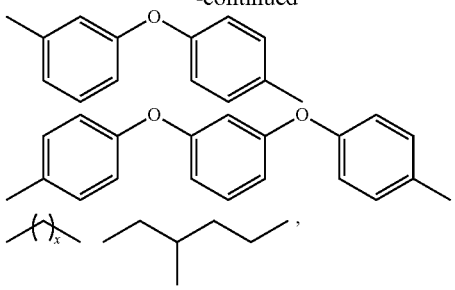

where w and x are each independently an integer from 1 to 20.

2. The blend of claim 1, having a viscosity ranging from 1 to $10^7$ cps at a temperature ranging from 0 to 50° C.

3. The blend of claim 1, wherein the vinyl monomer comprises a monomer selected from the group consisting of styrene, 2,3,4,5,6-pentafluoro styrene, divinyl benzene, methyl methacrylate, methyl acrylate, trifluoroacetic acid allyl ester, trifluoroacetic acid vinyl ester, 2,2,2-trifluoro-ethyl methacrylate, acrylic acid 1,1,1,3,3,3-hexafluoroiso-propyl ester, methacrylic acid 1,1,1,3,3,3-hexafluoroisopropyl ester, maleic anhydride, N-methyl maleimide, N-ethyl maleimide, N-propylmaleimide, N-butyl maleimide, N-tert-butyl maleimide, N-pentyl maleimide, N-hexyl maleimide and 1-pentafluorophenylpyrrole-2,5-dione.

4. A polymer sheet, comprising: a crosslinked product comprised of the blend of claim 1.

* * * * *